United States Patent [19]
Crocker et al.

[11] Patent Number: 5,843,116
[45] Date of Patent: *Dec. 1, 1998

[54] FOCALIZED INTRALUMINAL BALLOONS

[75] Inventors: Michael Crocker, Anaheim; Lynn M. Shimada, Irvine, both of Calif.

[73] Assignee: Cardiovascular Dynamics, Inc., Irvine, Calif.

[ * ] Notice: The term of this patent shall not extend beyond the expiration date of Pat. No. 5,470,313.

[21] Appl. No.: 742,437

[22] Filed: Oct. 30, 1996

Related U.S. Application Data

[63] Continuation-in-part of Ser. No. 670,683, Jun. 26, 1996, which is a continuation-in-part of Ser. No. 640,533, May 2, 1996, Pat. No. 5,645,560.

[51] Int. Cl.$^6$ .................................................. A61M 29/08
[52] U.S. Cl. .............................. 606/192; 606/108; 604/96
[58] Field of Search ..................................... 606/194, 192, 606/198, 108; 604/96

[56] References Cited

U.S. PATENT DOCUMENTS

| | | |
|---|---|---|
| 2,610,626 | 9/1952 | Edwards . |
| 3,701,351 | 10/1972 | Harvey . |
| 4,327,736 | 5/1982 | Inoue . |
| 4,733,665 | 3/1988 | Palmaz . |
| 4,762,130 | 8/1988 | Fogarty et al. . |
| 4,777,951 | 10/1988 | Cribier et al. . |
| 4,896,670 | 1/1990 | Crittendon . |
| 4,906,244 | 3/1990 | Pinchuk et al. . |
| 4,921,483 | 5/1990 | Wijay et al. . |
| 4,981,478 | 1/1991 | Evard et al. . |
| 4,983,167 | 1/1991 | Sanota . |
| 5,049,132 | 9/1991 | Shaffer et al. . |
| 5,074,845 | 12/1991 | Miraki et al. . |
| 5,108,369 | 4/1992 | Gangulu et al. . |
| 5,108,415 | 4/1992 | Pinchuk et al. . |
| 5,176,661 | 1/1993 | Evard et al. . |
| 5,195,969 | 3/1993 | Wang et al. . |
| 5,197,978 | 3/1993 | Hess . |
| 5,207,700 | 5/1993 | Euteneuer . |
| 5,219,355 | 6/1993 | Parodi et al. . |
| 5,222,966 | 6/1993 | Perkins et al. . |
| 5,246,421 | 9/1993 | Saab . |
| 5,250,069 | 10/1993 | Nobuyoshi et al. . |
| 5,250,070 | 10/1993 | Parodi . |
| 5,270,086 | 12/1993 | Hamlin . |
| 5,273,536 | 12/1993 | Savas . |
| 5,304,132 | 4/1994 | Jang . |
| 5,304,135 | 4/1994 | Shonk . |
| 5,308,356 | 5/1994 | Blackshear, Jr. et al. . |
| 5,320,634 | 6/1994 | Vigil et al. . |
| 5,338,298 | 8/1994 | McIntyre . |
| 5,342,301 | 8/1994 | Saab . |
| 5,342,305 | 8/1994 | Shonk . |
| 5,348,538 | 9/1994 | Wang et al. . |
| 5,352,199 | 10/1994 | Tower . |

(List continued on next page.)

FOREIGN PATENT DOCUMENTS

| | | |
|---|---|---|
| 0347023 | 4/1988 | European Pat. Off. . |
| 358117 | 3/1990 | European Pat. Off. . |
| 592885 | 4/1994 | European Pat. Off. . |
| 597465 | 5/1994 | European Pat. Off. . |
| 671883A5 | 10/1989 | Switzerland . |
| 94/02193 | 2/1994 | WIPO . |

*Primary Examiner*—Michael Powell Buiz
*Assistant Examiner*—Kevin Troung
*Attorney, Agent, or Firm*—Knobbe, Martens, Olson & Bear, LLP

[57] ABSTRACT

Disclosed is a focal balloon having at least one reference zone and a focal zone. In one embodiment, the reference zone and focal zone are inflatable to a first generally cylindrical profile at a first pressure. At a second, greater pressure, the focal section expands to a second, greater diameter, while the reference zone remains substantially at the first diameter. In an alternate embodiment, the focal zone and the reference zone are inflatable to their respective predetermined diameters at the inflation pressure, in the absence of constricting lesions or anatomical structures. Multiple lobed and drug delivery embodiments are also disclosed.

2 Claims, 12 Drawing Sheets

U.S. PATENT DOCUMENTS

| | | |
|---|---|---|
| 5,358,486 | 10/1994 | Saab . |
| 5,449,371 | 9/1995 | Pinchuk et al. . |
| 5,470,313 | 11/1995 | Crocker ..................................... 604/96 |
| 5,470,314 | 11/1995 | Walinsky . |
| 5,484,411 | 1/1996 | Inderbitzen et al. . |
| 5,514,073 | 5/1996 | Miyata et al. . |
| 5,632,762 | 5/1997 | Myler . |
| 5,749,851 | 5/1998 | Wang . |

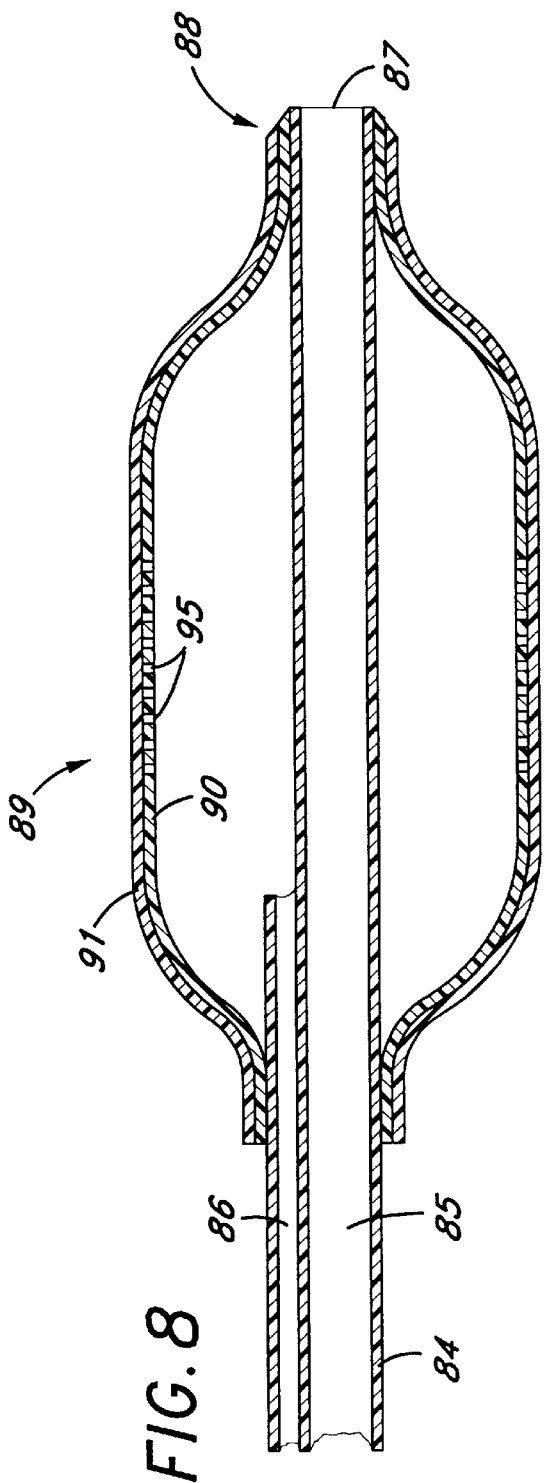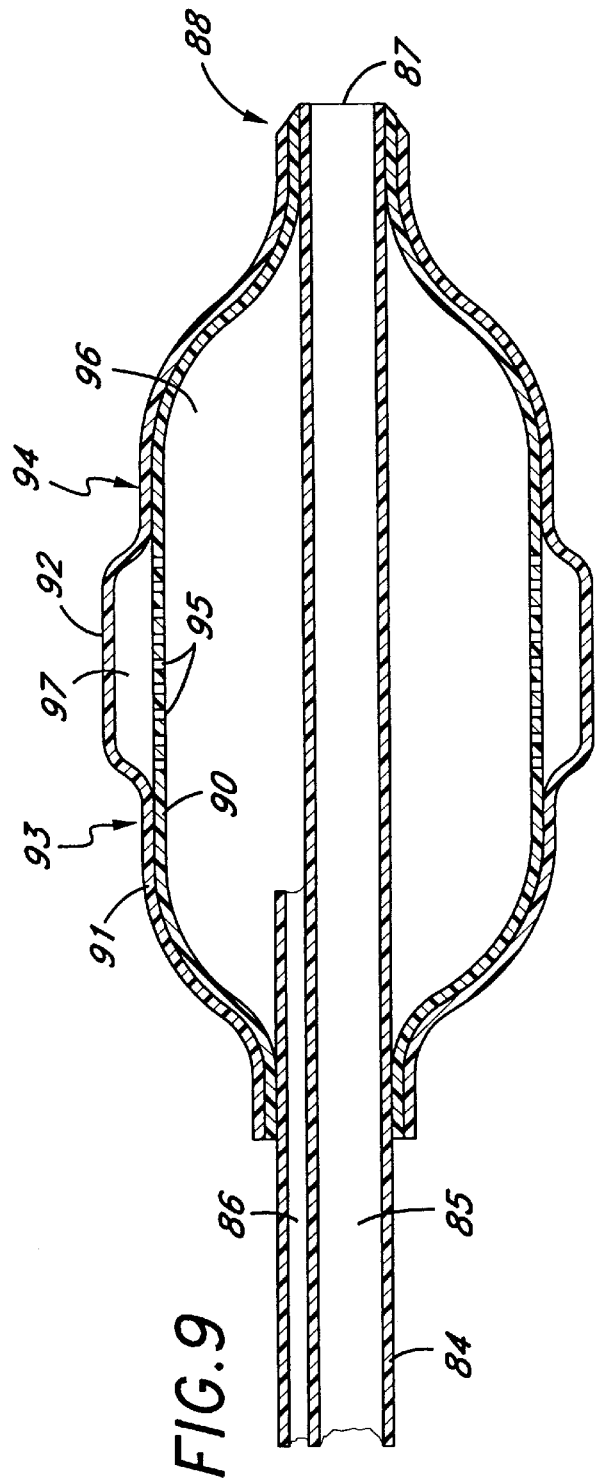

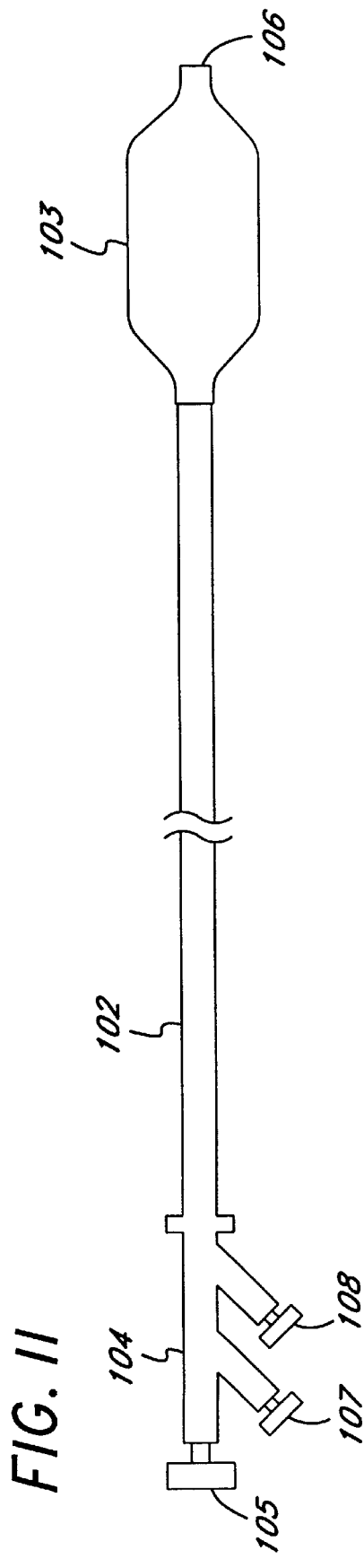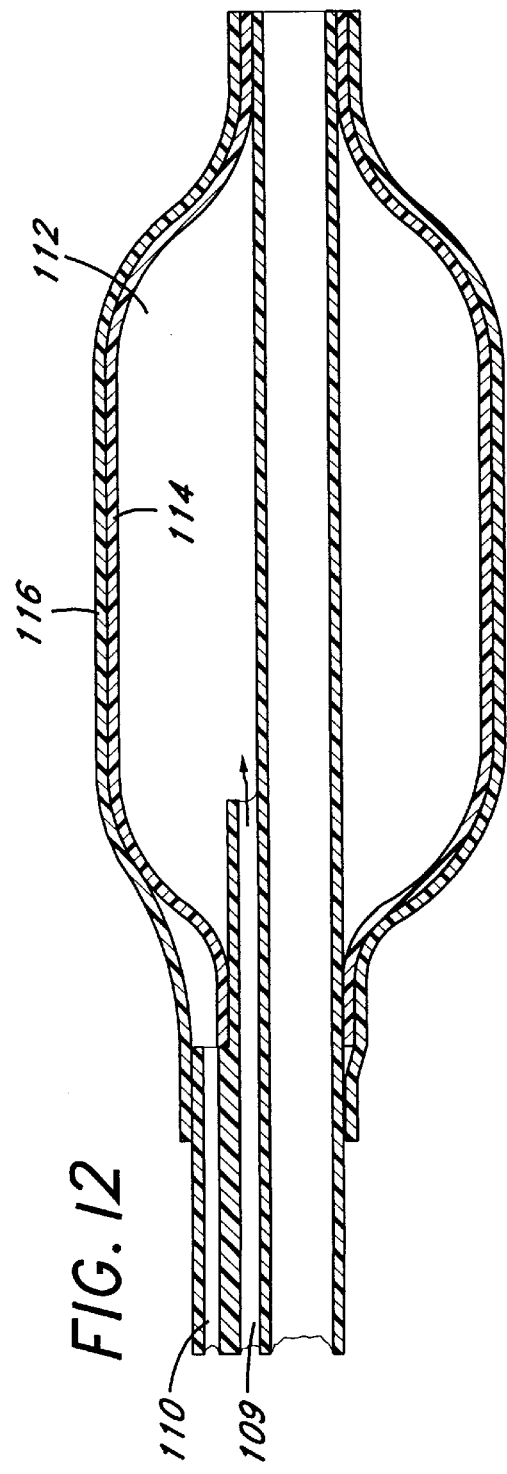

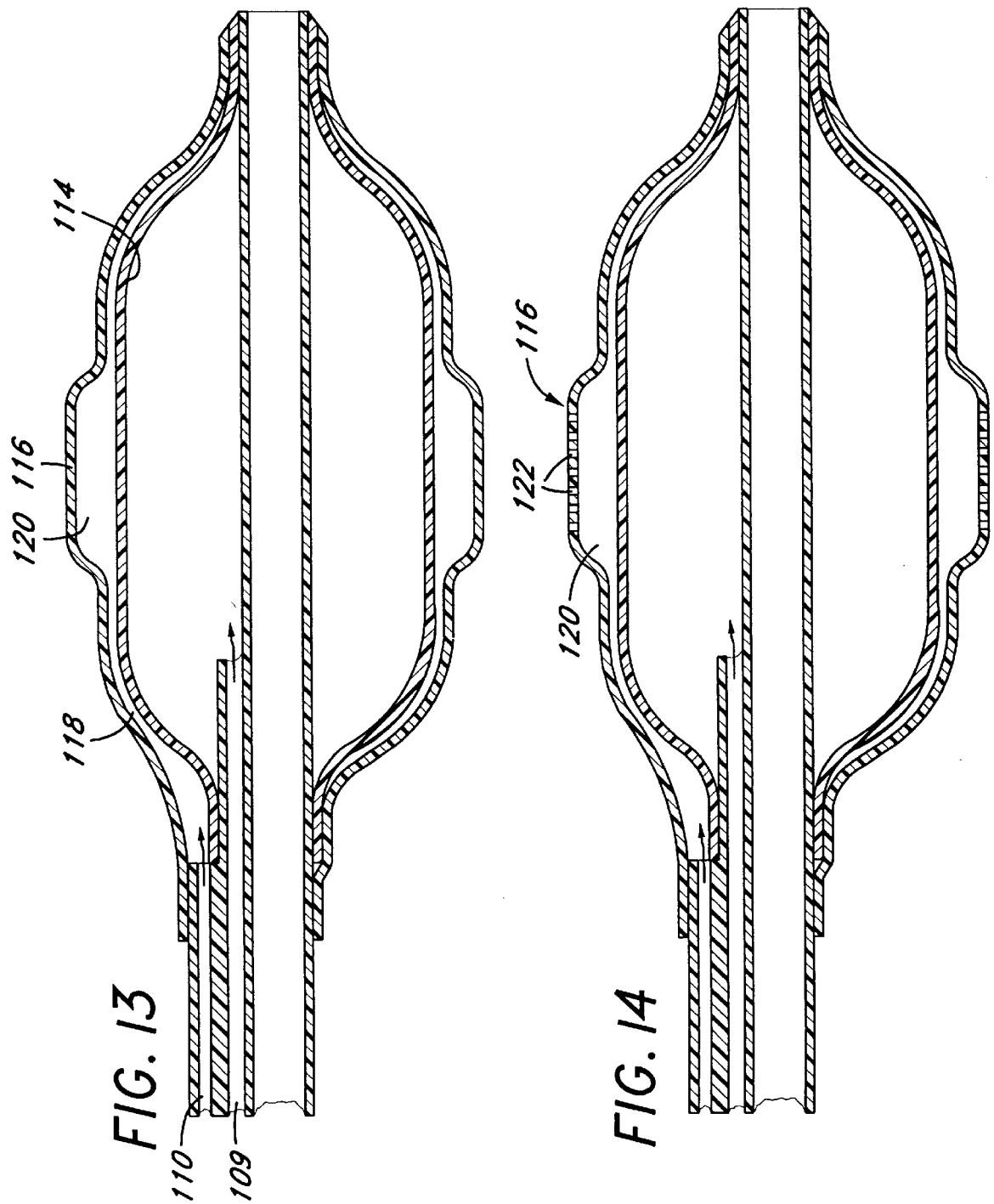

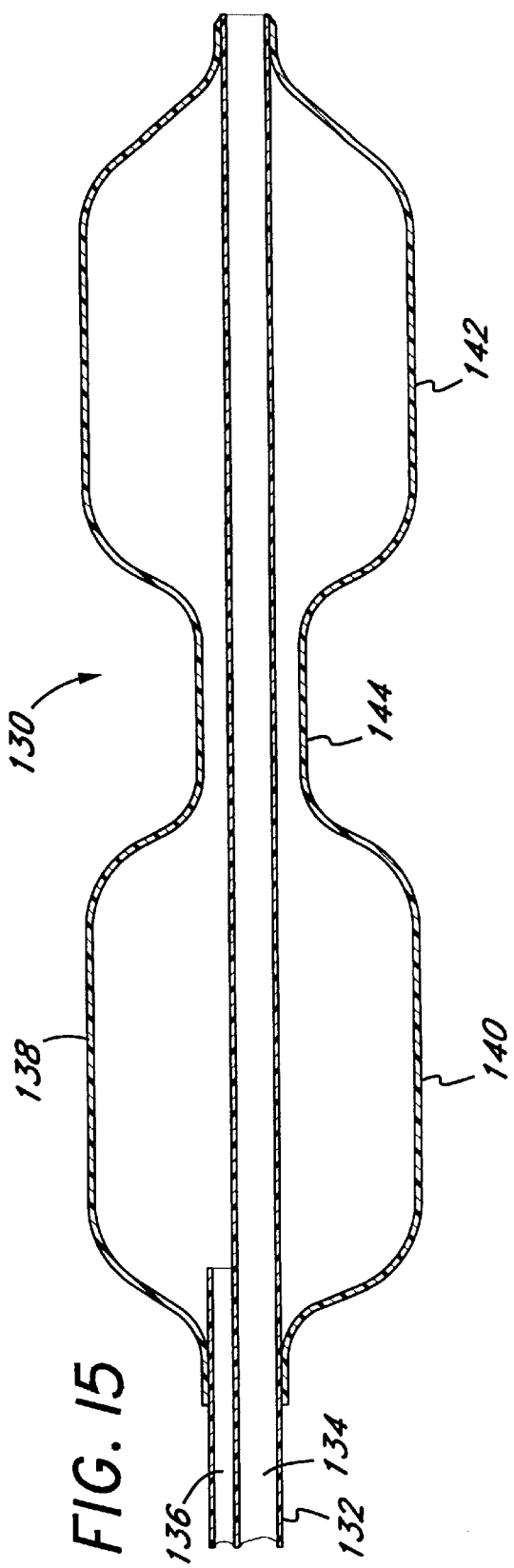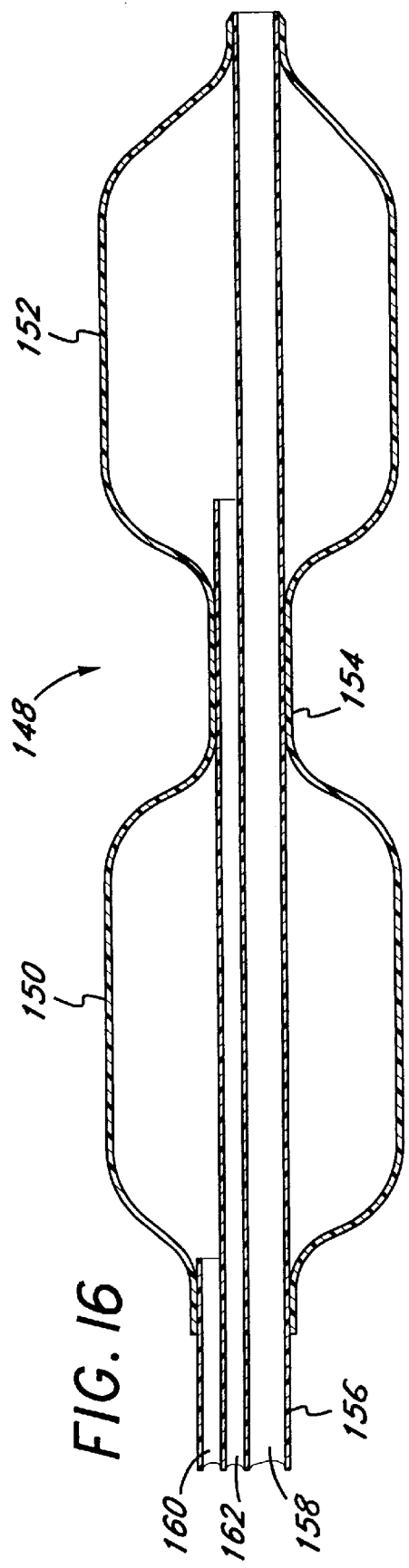

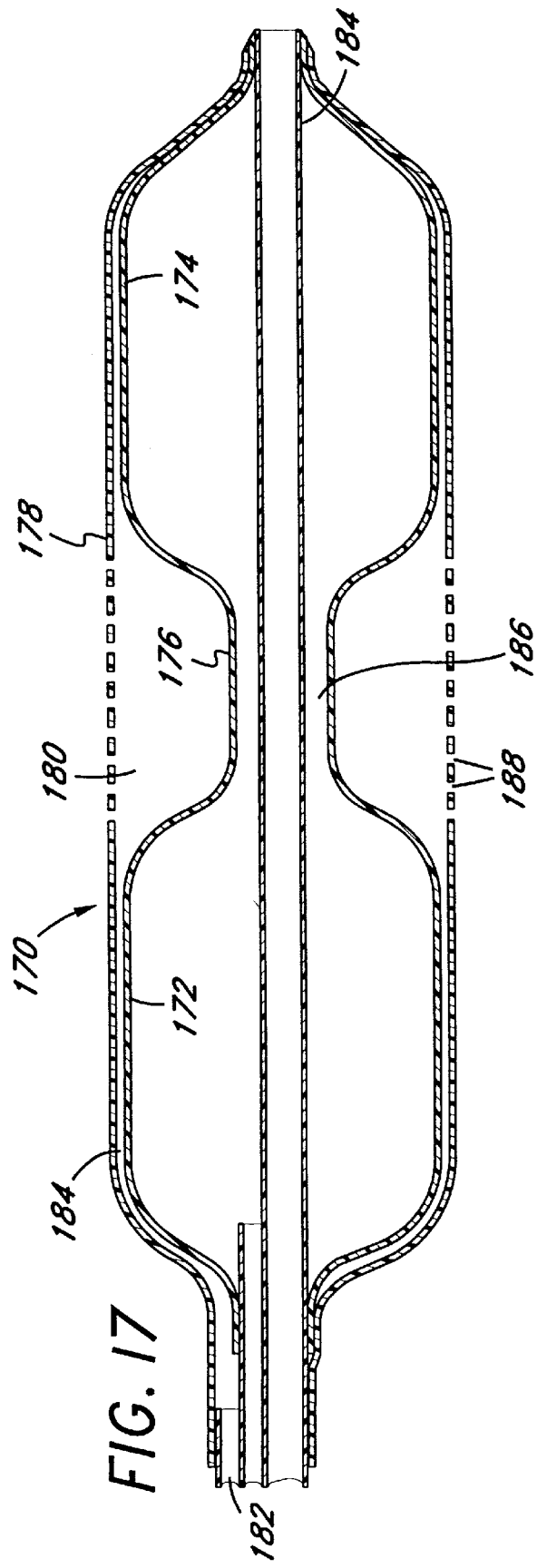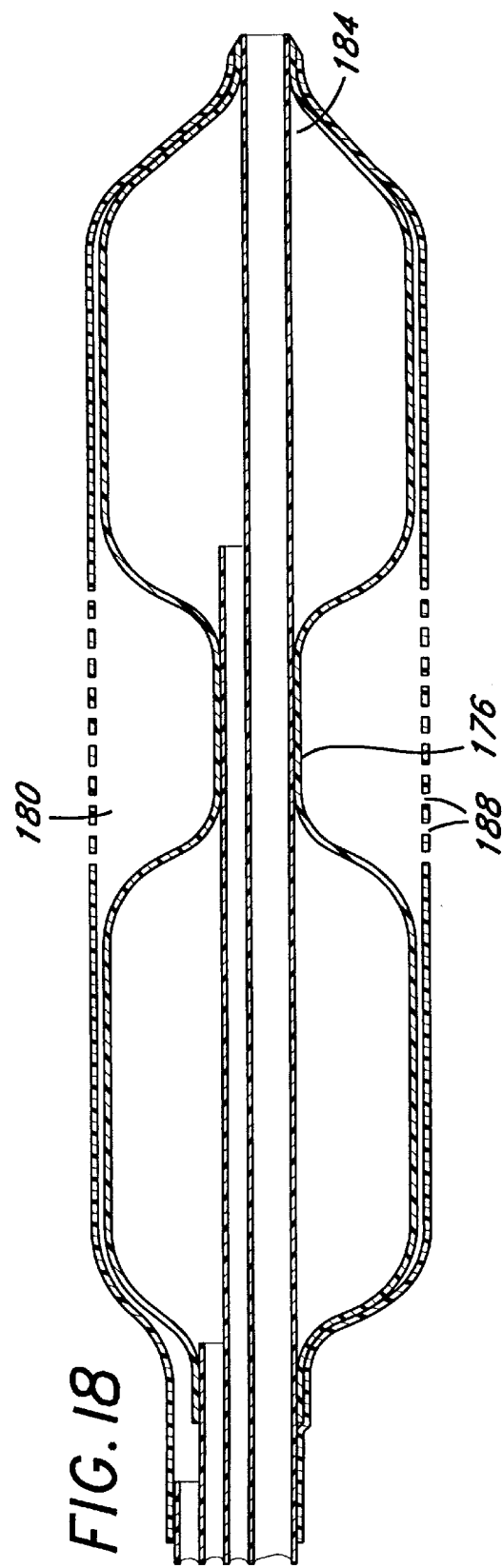

FOCALIZED INTRALUMINAL BALLOONS

The present application is a continuation-in-part of application Ser. No. 08/640,533, filed May 21, 1996 now U.S. Pat. No. 5,645,560 which is a continuation-in-part of copending application Ser. No. 08/670,683 filed Jun. 26, 1996, the disclosures of which are hereby incorporated herein by reference.

BACKGROUND OF THE INVENTION

The present invention relates to catheters for insertion into a body lumen. More particularly, the present invention relates to "focal" balloon dilatation catheters for use in the vascular system. As used herein, "focal" balloons are balloons which focus or concentrate expansive energy at one or more predetermined regions along the surface of the balloon.

Prior art vascular dilatation balloons on typical dilatation catheters tend to fall into one of two broad classes. Most are considered noncompliant balloons, formed from a generally nondistensible material such as polyethylene. The perceived advantage of the noncompliant balloons is that they exhibit a substantially uniform exterior inflated profile which remains substantially unchanged upon incremental increases in inflation pressure. In theory, noncompliant balloons are advantageous because they allow the introduction of increased inflation pressure to break particularly calcified lesions, yet retain a predictable inflated profile so that damage to the surrounding native lumen is minimized.

Certain compliant balloons are also known in the art. A compliant balloon is one which is able to grow in diameter in response to increased inflation pressure. One difficulty with compliant balloons, however, is that inflation within a difficult lesion can cause the balloon to inflate around the plaque to produce a generally hourglass-shaped inflated profile. This can result in damage to the native vessel adjacent the obstruction, while at the same time failing to sufficiently alleviate the stenosis.

In use, both the compliant and noncompliant balloons are generally inflated within a vascular stenosis to a rated inflation pressure. At that pressure, the configuration of most balloons in an unrestricted expansion is cylindrical. The balloon may be subsequently inflated to a higher inflation pressure if that is desirable in the clinician's judgment. However, the clinician has no effective way to assess the actual inflated diameter of the balloon in vivo based upon the unconstrained in vitro balloon specifications. The in vivo expansion characteristics of the balloon may track or deviate from the in vitro specifications depending upon the morphology of the lesion and the appropriateness of the selected balloon size. The clinician may know only generally or not at all the degree of calcification of the lesion, the symmetry or asymmetry, whether the lesion is soft or resilient, or other variations which affect inflation. In applications where a relatively accurate inflated diameter is desired, such as in certain dilatations or in the implantation of tubular stents, the clinician using prior dilatation balloons thus may not have enough information about the dilatation characteristics of a particular lesion to optimize the dilatation or stent implantation procedure.

Therefore, there exists a need in the art for a vascular dilatation catheter with a balloon which is able to grow predictably in response to increased inflation pressure, and the expansion of which the clinician can observe in real time in comparison to a known diameter reference.

SUMMARY OF THE INVENTION

There is provided in accordance with one aspect of the present invention a balloon catheter comprising an elongate flexible tubular body and an inflatable balloon on the tubular body. A proximal segment, a central segment and a distal segment on the balloon are inflatable to a first inflated diameter at a first inflation pressure, and the proximal and distal segment expand to a second, greater inflated diameter at a second greater inflation pressure. The central segment of the balloon remains at a diameter which is less than the second diameter, at the second inflation pressure. In one embodiment, the balloon additionally comprises at least one expansion limiting band on the central segment to limit inflation of the central segment of the balloon. Preferably, the expansion limiting band limits expansion of the central segment to no more than about the first inflated diameter.

In accordance with another aspect of the present invention, there is provided a method of treating a site in a body lumen. The method comprises the steps of providing a catheter of the type having an elongate flexible tubular body and a dilatation balloon on the body. A proximal segment, a distal segment and a central segment of the balloon are inflatable to a first diameter at a first inflation pressure, and the proximal and distal segments of the balloon are inflatable to a second, greater diameter, at a second, greater inflation pressure. The central segment remains substantially at the first diameter at said second inflation pressure.

The catheter is positioned within a body lumen so that the balloon is adjacent a treatment site, and the balloon is inflated to the first inflation pressure. At the first inflation pressure, the proximal segment, the distal segment and the central segment are inflated to no more than about the first inflation diameter. The balloon is thereafter inflated to a second inflation pressure so that the proximal and distal segments are expanded to the second inflation diameter, while the central segment is simultaneously restrained against further material radial expansion.

Optionally, the foregoing method comprises the additional step of expressing a therapeutic or diagnostic media from the central segment of the balloon to the site in the body lumen.

In accordance with a further aspect of the present invention, there is provided a method of implanting a tubular graft within a body lumen. The method comprises providing an elongate flexible tubular body having an inflatable balloon thereon, the balloon inflatable to a first diameter at a first inflation pressure to produce a generally cylindrical balloon profile, and proximal and distal portions of the balloon are additionally inflatable to a second, larger diameter at a second, greater inflation pressure. An expandable tubular graft is positioned on the balloon, and the balloon is thereafter positioned within a body lumen adjacent a treatment site.

The balloon is inflated to the first inflation diameter to expand the tubular graft and thereafter inflation pressure is increased to the second inflation pressure such that the proximal and distal portions of the balloon inflate to the second, larger diameter, to further expand the proximal and distal portions of the tubular graft.

Further features and advantages of the present invention will become apparent to one of skill in the art in view of the Detailed Description of Preferred Embodiments which follows, when considered together with the attached drawings and claims.

BRIEF DESCRIPTION OF THE DRAWINGS

FIG. 8 is a cross sectional view through a dual layer balloon having a central compliant zone thereon.

FIG. 9 is a cross sectional view as in FIG. 8, with the compliant zone in the expanded configuration.

FIG. 11 is a schematic elevational view of a dual inflation lumen catheter.

FIG. 12 is a cross sectional view through a dual layer balloon having a unique inflation lumen for each layer.

FIG. 13 is a cross sectional view of a dual layer balloon as in FIG. 12, in the focalized configuration.

FIG. 14 is a cross sectional view through a balloon similar to that in FIG. 13, but with added delivery capability.

FIG. 15 is a cross sectional schematic illustration of a balloon having a proximal and a distal lobe.

FIG. 16 is a cross sectional schematic illustration of a dual balloon configuration.

FIG. 17 is a cross sectional illustration of a dual lobed balloon adapted for delivery of media into the vessel.

FIG. 18 is a cross sectional view of a dual balloon catheter, configured for delivery of media into the vessel.

DETAILED DESCRIPTION OF THE PREFERRED EMBODIMENTS

Figure 1:
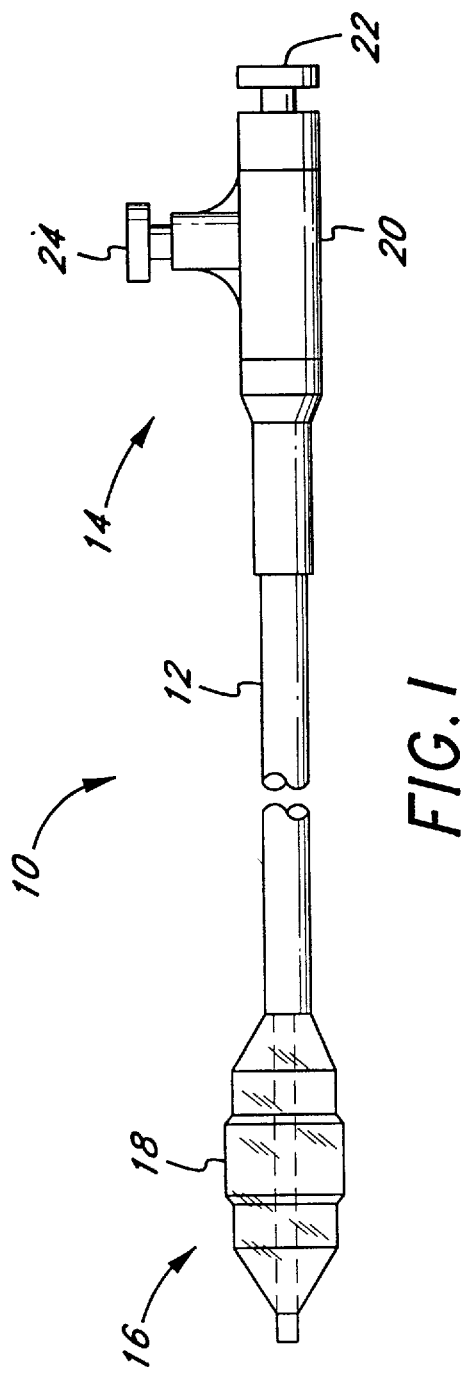
FIG. 1 is a schematic view of a preferred embodiment of a variable diameter inflation catheter of one aspect of the present invention, in the second inflation configuration.
Figure 4:
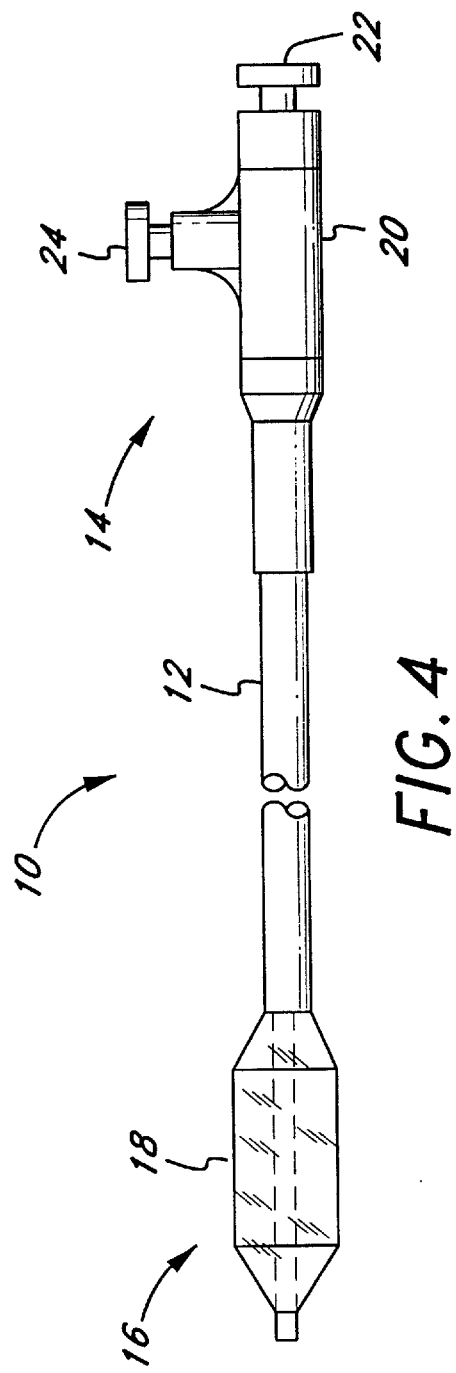
FIG. 4 is a schematic view of the embodiment of FIG. 1, shown in the first inflation configuration.

Referring to FIG. 1, there is disclosed a variable diameter inflation catheter 10 in accordance with of one aspect of the present invention. Catheters embodying additional features known in the vascular dilatation art, such as implantable stents, drug delivery, perfusion and dilatation features, or any combination of these features, can be used in combination with the focal balloon of the present invention as will be readily apparent to one of skill in the art in view of the disclosure herein.

The catheter 10 generally comprises an elongate tubular body 12 extending between a proximal control end 14 and a distal functional end 16. The length of the tubular body 12 depends upon the desired application. For example, lengths in the area of about 120 cm to about 140 cm are typical for use in percutaneous transluminal coronary angioplasty applications.

The tubular body 12 may be produced in accordance with any of a variety of known techniques for manufacturing balloon-tipped catheter bodies, such as by extrusion of appropriate biocompatible plastic materials. Alternatively, at least a portion or all of the length of tubular body 12 may comprise a spring coil, solid walled hypodermic needle tubing, or braided reinforced wall, as is understood in the catheter and guide wire arts.

In general, tubular body 12, in accordance with the present invention, is provided with a generally circular cross-sectional configuration having an external diameter within the range of from about 0.03 inches to about 0.065 inches. In accordance with one preferred embodiment of the invention, the tubular body 12 has an external diameter of about 0.042 inches (3.2 f) throughout most of its length. Alternatively, generally triangular or oval cross-sectional configurations can also be used, as well as other non-circular configurations, depending upon the number of lumen extending through the catheter, the method of manufacture and the intended use.

In a catheter intended for peripheral vascular applications, the tubular body 12 will typically have an outside diameter within the range of from about 0.039 inches to about 0.065 inches. In coronary vascular applications, the tubular body 12 will typically have an outside diameter within the range of from about 0.026 inches to about 0.045 inches. Diameters outside of the preferred ranges may also be used, provided that the functional consequences of the diameter are acceptable for the intended purpose of the catheter. For example, the lower limit of the diameter for tubular body 12 in a given application will be a function of the number of fluid or other functional lumen, support structures and the like contained in the catheter, and the desired structural integrity.

Tubular body 12 must have sufficient structural integrity (e.g., "pushability") to permit the catheter to be advanced to distal arterial locations without buckling or undesirable bending of the tubular body 12. The ability of the body 12 to transmit torque may also be desirable, such as in embodiments having a drug delivery capability on less than the entire circumference of the delivery balloon. Larger diameters generally have sufficient internal flow properties and structural integrity, but reduce perfusion in the artery in which the catheter is placed. Increased diameter catheter bodies also tend to exhibit reduced flexibility, which can be disadvantageous in applications requiring placement of the distal end of the catheter in a remote vascular location. In addition, lesions requiring treatment are sometimes located in particularly small diameter arteries, necessitating the lowest possible profile.

As illustrated schematically in FIG. 1, the distal end 16 of catheter 10 is provided with at least one inflation balloon 18 having a variable diameter. The proximal end 14 of catheter 10 is provided with a manifold 20 having a plurality of access ports, as is known in the art. Generally, manifold 20 is provided with a guide wire port 22 in an over the wire embodiment and a balloon inflation port 24. Additional access ports are provided as needed, depending upon the functional capabilities of the catheter 10. The balloon 18 can also be mounted on a rapid exchange type catheter, in which the proximal guidewire port 22 would be unnecessary as is understood in the art. In a rapid exchange embodiment, the proximal guidewire access port is positioned along the length of the tubular body 12, such as between about 4 and about 20 cm from the distal end of the catheter.

Figure 2:
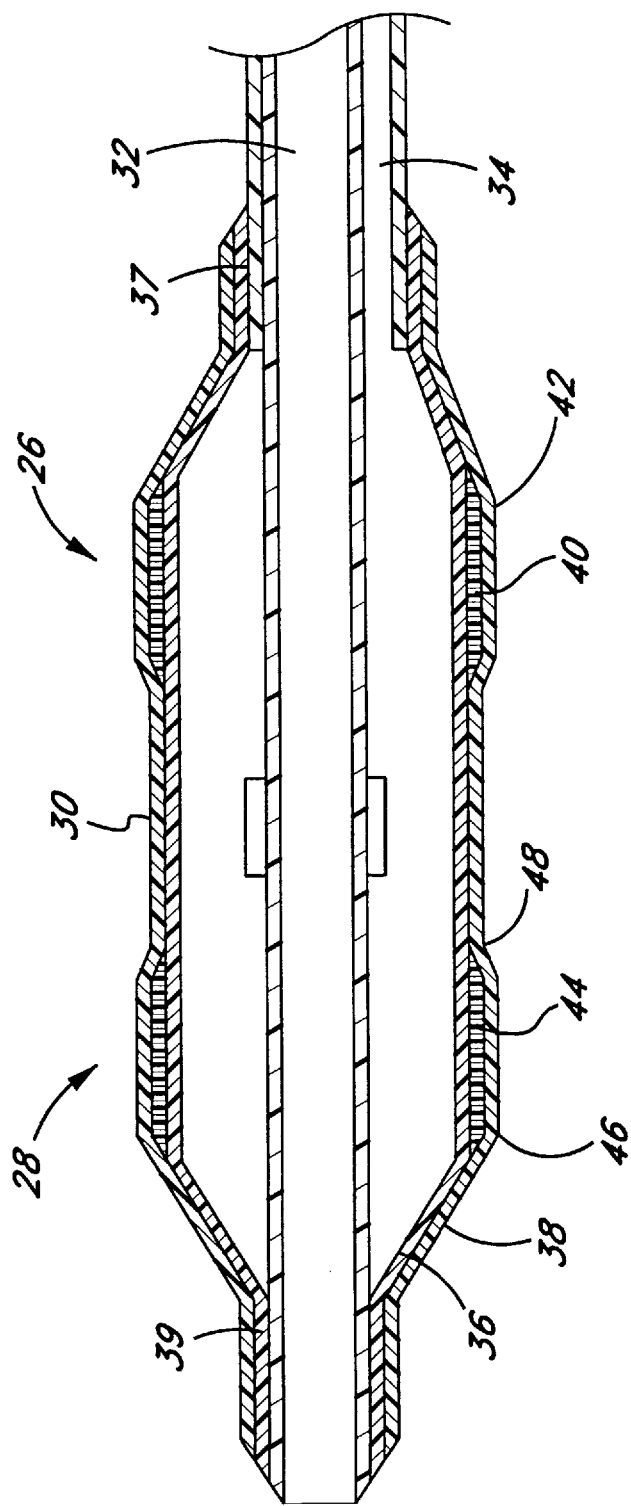
FIG. 2 is a partial cross-sectional view of a preferred embodiment of the variable diameter inflation catheter at a first inflation profile.
Figure 3:
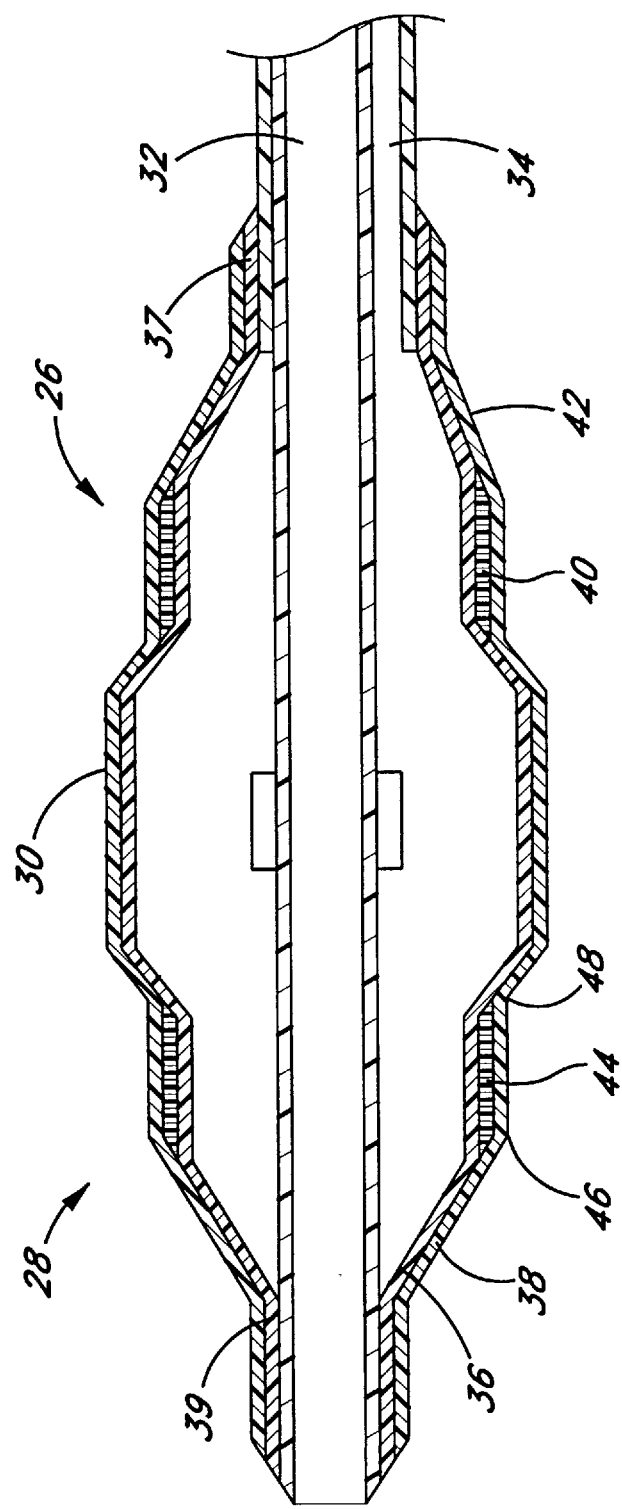
FIG. 3 is a partial cross-sectional view of a preferred embodiment of the variable diameter inflation catheter at a second inflation profile.

Referring to FIGS. 2 and 3, the two-step inflation profile of the inflation balloon 18 is illustrated. In FIG. 2, the balloon 18 is illustrated at a first inflation profile, in which in an unconstrained expansion it exhibits a substantially cylindrical central working profile. The dimensions in FIG. 2 are exaggerated to illustrate a proximal segment 26 and a distal segment 28 which are axially separated by a central focal segment 30. However, as will be understood by one of ordinary skill in the art, when the balloon 18 is inflated to the first inflation profile, the exterior of the balloon 18 preferably exhibits a substantially smooth cylindrical working profile.

In FIG. 3, the inflation balloon 18 is illustrated at a second inflation profile. The proximal segment 26 and the distal segment 28 of the balloon are separated by the central focal segment 30 having a greater diameter. The configuration of FIG. 2 is achieved by inflating the balloon 18 to a first inflation pressure, while the configuration of FIG. 3 is achieved by increasing the inflation pressure to a second, higher pressure as will be discussed below.

The details of one preferred embodiment of the variable diameter inflation catheter 10 are discussed with reference to FIGS. 2 and 3. Preferably, the tubular body 12 is provided with at least a guidewire lumen 32 extending all the way through the balloon 18, and an inflation lumen 34 extending into the proximal end of the balloon 18.

In the illustrated embodiment, an inner balloon 36 is disposed coaxially within an outer balloon 38. A substantially nondistensible expansion limiting band 40 is disposed in between the balloons 36 and 38 adjacent a proximal annular shoulder 42, to limit the radial expansion of the balloon 18. Similarly, a distal expansion limiting band 44 is disposed between the inner balloon 36 and outer balloon 38 adjacent a distal annular shoulder 46.

Expansion limiting bands 40 and 44 or other inflation limiting structures can be provided in any of a variety of ways which will be well-understood by one of skill in the art in view of the disclosure herein. For example, in one embodiment, the bands 40 and 44 each comprise a tubular section of polyester, each having an axial length of about 5 mm, a diameter of about 2.5 mm and a wall thickness of about 0.0003 inches. Other generally nondistensible materials such as nylon, polyamide, Kevlar fiber, cross-linked polyethylene, polyethylene terephthalate and others, may be utilized to accomplish the expansion-limiting effect.

The expansion limiting characteristics can be achieved by the addition of a structure that is discrete from the balloon, or by modifying the expansion properties of the balloon material itself. For example, the balloon can be provided with zones of differing wall thickness, or zones having different levels of cross linking as will be discussed.

In general, the bands 40 and 44 must be of a sufficient thickness or structural integrity for the particular material used to substantially withstand inflation under the pressures normally utilized in the context of dilatation catheters. However, the bands 40 and 44 are preferably thin enough to provide a substantially smooth exterior surface of the balloon 18.

Preferably, as illustrated in FIGS. 2 and 3, the expansion-limiting bands 40 and 44 are sandwiched between the inner balloon 36 and the outer balloon 38. In alternative embodiments, the expansion-limiting bands 40 and 44 or other inflation limiting structures may be coated or mounted on the exterior surface of the balloon 18, the interior surface of the balloon 18 or within the wall of the balloon 18. Balloon 18 can be provided with two or more layers as illustrated, or with only a single layer as will be discussed.

The axial length of the bands 40 and 44 can be varied widely depending upon the dimensions and the objectives of the catheter 10 as will be apparent to one of ordinary skill in the art. Further, the proximal band 40 and distal band 44 need not be of similar lengths. In general, however, some examples of dimensions which are useful in the coronary angioplasty dilatation environment are reproduced in Table 1 below, in which A represents the axial length of the balloon 18 between proximal shoulder 42 and distal shoulder 46, B represents the axial distance between distal shoulder 46 and transition point 48, and C represents the axial length of the central focal segment 30. The dimensions of Table 1 are exemplary only, and the present invention can be accomplished using a wide variety of other dimensions as will be apparent to one of skill in the art.

TABLE 1

| A | B | C |
|---|---|---|
| 20 mm | 5 mm | 10 mm |
| 30 mm | 5 mm | 20 mm |
| 40 mm | 5–10 mm | 20–30 mm |

The catheter 10 illustrated in FIGS. 2 and 3 can be manufactured in accordance with any of a variety of techniques which will be appreciated by one of ordinary skill in the art in view of the disclosure herein. In the following disclosure, particular materials and dimensions will be used as an example only, and other dimensions and materials can be selected depending upon the desired characteristics of the finished product.

In one particular method of manufacturing, a low density polyethylene extrusion stock tube having an inside diameter of about 0.018 inches and an outside diameter of about 0.043 inches is used for the inner and outer balloons 36, 38.

The polyethylene stock tubing is cross-linked by exposure to an electron beam in accordance with techniques well known in the art. A test segment of the cross-linked stock tubing is free blown up to 3.0 mm in diameter. If the cross-linked stock tubing can be free blown to a diameter greater then 3.0 mm, the stock tubing is cross-linked again and retested until the desired free blow diameter is achieved.

The appropriately cross-linked stock tubing is then blown to a diameter of 2.5 mm within a teflon capture tube (not shown) which acts to mold the balloon to its desired first inflation diameter. The teflon capture tube is a generally tubular body which has approximately the same inside diameter as the desired inflation diameter of the balloon. The teflon capture tube is heated by any of a number of heating means such as electric coils or a furnace to a temperature which is sufficient to mold the balloon to the desired inflation diameter. In this case, the cross-linked polyethylene balloon is preferably heated to a temperature of about 300° F. The teflon chamber is then cooled to a temperature below the softening temperature of the balloon. Once cooled, the balloon is deflated and removed from the capture tube.

A section of inflation balloon material is thereafter stretched with application of heat to neck down the proximal and distal ends 37, 39 to a thickness of about 0.001 inches and a diameter which relatively closely fits the portion of the tubular catheter body 12 to which it is to be sealed.

The balloon is then attached to the tubular body 12 by any of a variety of bonding techniques known to one of skill in the art such as solvent bonding, thermal adhesive bonding or by heat shrinking/sealing. The choice of bonding techniques is dependent on the type of balloon material and tubular body material used to form the catheter 10.

In one particular method of manufacture, inner balloon 36 and outer balloon 38 are attached to the catheter body 10. The proximal necked end 37 of the inner balloon 36 is heat sealed around the catheter body 12. The distal necked end 39 of the inner balloon 36 is thereafter heat sealed around the distal end 16 of the catheter body 12. In general, the length of the proximal end 37 and the distal end 39 of the inner balloon 36 which is secured to the catheter body 12 is within the range of from about 3 mm to about 10 mm, however the proximal and distal balloon necked ends 37, 39 are as long as necessary to accomplish their functions as a proximal and distal seal.

Expansion limiting bands 40 and 44 are respectively positioned at the proximal segment 26 and the distal segment 28 of the inner balloon 36 and may be bonded or otherwise secured to the inner balloon 36. The outer balloon 38 is thereafter be mounted to the catheter body 12 in a similar manner as the inner balloon 36, following "necking down" of the proximal and distal axial ends of the outer balloon 38 by axial stretching under the application of heat. The outer balloon 38 is advanced axially over the inner balloon 36 and the expansion limiting bands 40 and 44. The outer balloon 38 may thereafter be bonded to the inner balloon 36, and to the expansion limiting bands 40 and 44 by any of a variety of bonding techniques such as solvent bonding, thermal adhesive bonding or by heat sealing also depending on the type of balloon material used. Alternatively, the expansion limiting bands are simply entrapped between the balloons without any bonding or adhesion.

In a preferred embodiment, the inner balloon and the outer balloon 36, 38 are both cross-linked polyethylene balloons which are difficult to bond together using conventional solvents. If sealing is desired, the inner balloon 38 and the outer balloon 38 are heat sealed together as described below. In another embodiment, the inner balloon 36 and outer balloon 38 are secured together through the use of a UV-curable adhesive.

The inner balloon 36 and the outer balloon 38, once mounted to the catheter body 12, can be heat sealed together in a heating chamber (not shown) such as a Teflon capture tube. Inner balloon 36 and outer balloon 38 are inflated in the chamber until the inner balloon and the outer balloon inflate to the first inflation diameter. The heating chamber is heated by any of a number of heating means such as electric coils or a furnace to heat air to a temperature which is sufficient to bond the two balloons 36, 38 together. In this case, the cross-linked polyethylene balloons are preferably heated to a temperature of about 300° F. within the chamber which causes both balloons 36, 38 to seal together to form a double walled variable diameter inflation balloon 18. The chamber is then cooled to a temperature below the softening temperature of the inner and outer balloons 36 and 38. Once cooled, the variable diameter balloon 18 is deflated and the catheter 10 is removed from the chamber.

It will be apparent to one of skill in the art, that it is possible to attach the inner balloon 36 and the outer balloon 38 to the catheter body 12 without adhesively bonding or otherwise securing the two balloons together. In this case, the two balloons will respond to the applied inflation pressure with the inner balloon 36 forcing the outer balloon 38 to simultaneously inflate both balloons 36, 38. The expansion limiting bands 40 and 44 can be merely sandwiched between the inner balloon 36 and the outer balloon 38 and do not in this embodiment need to be bonded to either balloon.

The variable diameter balloon design of the present invention can also be accomplished with a single layer balloon or a double layer balloon without the inclusion of additional expansion limiting bands. This is accomplished by decreasing the relative compliance of the zones of the balloon that are intended to remain at the first inflated diameter. Alternatively, the compliance of the focal section can be increased relative to that of the reference zones.

For example, polyethylene extrusion stock is cross-linked to 3.0 mm and blown into a mold of a diameter of about 2.5 mm as described above to form a balloon. Balloon stock can be crosslinked either before or after mounting on the catheter, and in either the inflated or deflated state. The proximal and distal segments 26, 28 of the balloon on the catheter 10 are masked such as with steel clamps or other masks known in the art to block electron beam penetration, leaving the central segment 30 of the balloon exposed. The central segment 30 of the balloon 18 is exposed again to an electron beam source to be further cross-linked at the 2.5 mm diameter. Balloons manufactured in this manner have been found to exhibit a relatively highly compliant central zone and relatively less complaint axial end zones in a manner that achieves the two-step dilatation as illustrated in FIGS. 2 and 3.

Figure 6:
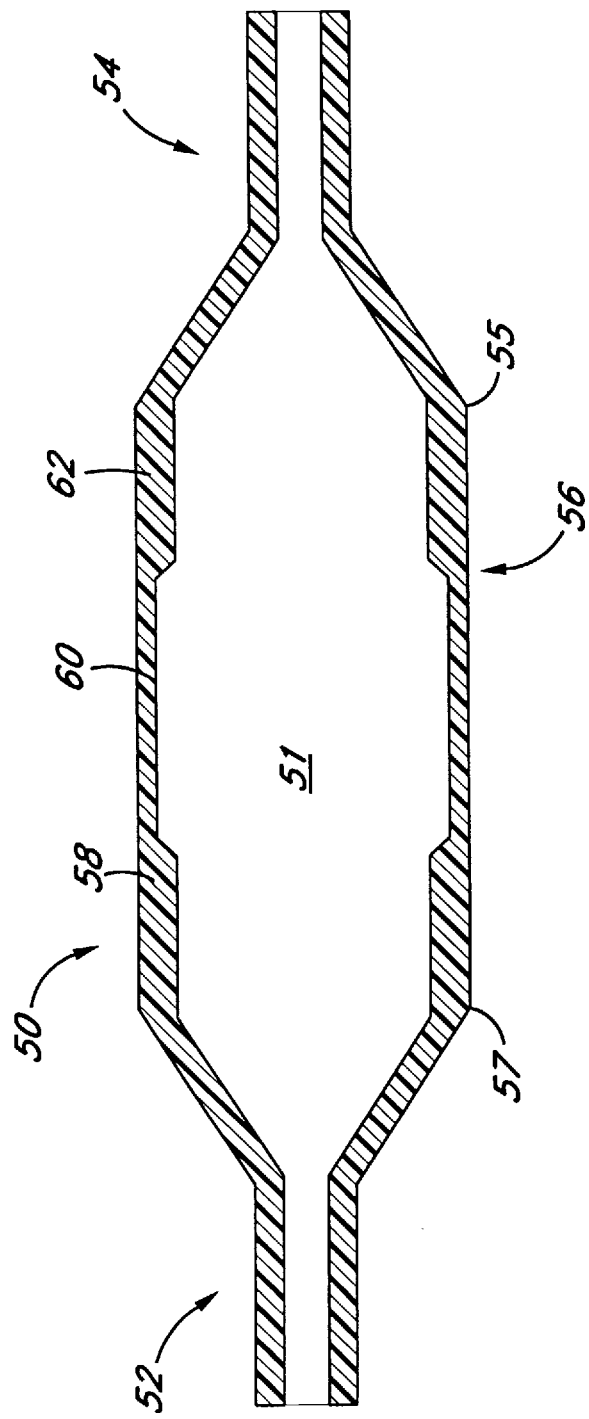
FIG. 6 is a schematic illustration of a balloon of the present invention having a relatively thin wall in the focal section.

Single layer balloons having the differential compliancy characteristics described above can also be provided using other balloon materials such as polyethylene terephthalate (PET). For example, a one piece single layer PET balloon can be provided with a thinner wall in the focal section compared to the one or two reference sections of the balloon. FIG. 6 discloses a schematic illustration of a balloon 50 in accordance with this aspect of the present invention. The balloon 50 defines an interior space 51 for containing inflation media as is understood in the art. The balloon 50 generally comprises a distal neck portion 52 and proximal neck portion 54 for securing the balloon 50 to the catheter. A working length of the balloon 56 extends between proximal shoulder 55 and distal shoulder 57.

The working length 56 of the balloon 50 is provided with a proximal reference zone 62 and a distal reference zone 58, separated by a focal zone 60. As has been discussed in connection with previous embodiments, the balloon 50 can alternately be provided with only a single reference zone either 58 or 62, together with the focal zone 60. Preferably, however, both proximal and distal reference zones 62 and 58 will be utilized with a central focal zone 60.

The thickness of at least a portion of the balloon wall in the area of focal zone 60 is thinner than the wall thickness in the reference zones 62 and 58.

In one embodiment of the single wall focal balloon of the present invention, the balloon comprises PET. The balloon has a working length of about 20 mm, and the proximal and distal reference zones 62 and 58 each have a length of about 5 mm. The focal zone 60 has a length of about 10 mm. The first inflated diameter at 8 ATM is about 3.0 mm, and the focal section inflates in vitro to about 3.5 mm at 16 ATM. The wall thickness in the area of reference zones 62 and 58 is about 0.001 inches, and the wall thickness in the area of focal zone 60 is about 0.0007 inches.

Whether the balloon comprises PET or other balloon materials known in the art, a thinner focal section compared to the thickness at the reference section can be provided using a variety of techniques. For example, the PET balloon can be exposed to heat and stretched in the center portion to provide a relatively thinner wall than the end reference portions. Alternatively, the balloon can be heated at its ends to shrink the balloon thereby increasing the thickness of the material in the regions exposed to heat.

Thinning a portion of the wall of the balloon by stretching the material can be accomplished in any of a variety of ways that will be apparent to those of skill in the art, in view of the disclosure herein. One method of reducing the wall thickness in the region of the focal zone involves an axial elongation of the tubular balloon stock under the application of heat. In general, the present inventor has found that the percent reduction in wall thickness is roughly equivalent to the percent axial elongation of the tubular stock. Thus, the tube stock is axially elongated a sufficient distance to achieve the desired reduction in wall thickness.

In one application of the invention, a molded PET balloon having a wall thickness of about 0.001 inches was axially elongated a sufficient distance to reduce the focal zone thickness to about 0.0007 inches. A molded PET balloon having a wall thickness of about 0.0008 inches was axially elongated by 40% to produce a wall thickness of about 0.0005 inches.

In one application of the method of the invention, a length of tubular polymeric stock is provided. The stock may be cut to a useful working length, such as 10–20 centimeters. Excess stock length following the elongation process will be trimmed prior to mounting of the balloon on the catheter shaft as will be understood by those of skill in the art.

A 15 cm length of PET balloon tubing having a wall thickness of about 0.0010 inches and an inflated outside diameter of about 3.0 mm was clamped at or near each end in a device configured to apply an axially stretching force to the tubing. Prior to closing one of the clamps, a needle was advanced through the open end of the tubing so that the tubing can be pressurized following clamping. Following clamping, the tubing was inflated under a pressure of about 100 psi, and axial tension in the area of about 1 lb. was applied.

The foregoing setup for a 3 mm balloon was accomplished inside of a 3 mm capture tube. First and second aluminum heat sinks were thermally coupled to the capture tube, and spaced about 5 mm apart. A hot air heater having a length of about 5 mm in the axial tube direction was positioned in between the heat sinks and advanced towards the capture tube to heat the capture tube. The heat sinks assist in localizing the region of the tubing stock which will be heated by the heater, as will be understood by those of skill in the art.

Upon reaching a temperature of about 200° F., the tube stock begins to stretch under the axial tension. The axial length of travel of the stretching clamps is preferably limited to provide a predetermined limit for the percentage axial elongation. In one application of the invention, the 5 mm heated section grew to about 5 or 7 mm in axial length following a 20%–40% increase in the distance between the clamps. Any of a variety of modification to the foregoing procedure can be readily envisioned by those of skill in the art. For example, alternate sources of heat such as forced air heating, infra red, electrical coil, and others known in the art can be used. In addition, stretching can be accomplished through any of a variety of physical setups, which can be readily assembled by those of skill in the art. Stretching without the application of heat, such as by cold rolling or cold forming a portion of tubular stock may also provide an acceptable thinning of the balloon wall for certain types of balloon materials.

Subject to the pressure retention characteristics of bonds between dissimilar balloon materials, the balloon can alternatively be provided with a relatively more compliant material in a focal section, and a relatively less compliant material in a reference section. Balloons having a combination of materials having different compliancies can be manufactured, for example, using two extrusion heads which alternately drive balloon material through a single orifice. Any of a variety of material pairs may be used, such as nylons of different hardness, PET and PE, and others that can be selected by those skilled in the art. As a further alternative, the focal section can be formed from an entirely different balloon which is positioned adjacent a single reference balloon or positioned in between two reference balloons to produce a balloon having some of the characteristics of the focal balloon of the present invention.

Balloons 18 made in accordance with the design illustrated in FIGS. 2 and 3 have been found to exhibit the inflation pressure profile illustrated in Table 2.

TABLE 2

| PRESSURE | CENTRAL SEGMENT DIAMETER | PROXIMAL AND DISTAL SEGMENT DIAMETER |
| --- | --- | --- |
| 6 atm | 2.5 mm | 2.5 mm |
| 7 atm | 2.6 mm | 2.5 mm |
| 8 atm | 2.7 mm | 2.5 mm |
| 9 atm | 2.8 mm | 2.5 mm |
| 10 atm | 2.9 mm | 2.6 mm |
| 11 atm | 3.0 mm | 2.6 mm |
| 12 atm | 3.1 mm | 2.7 mm |
| 13 atm | 3.2 mm | 2.7 mm |
| 14 atm | 3.2 mm | 2.7 mm |

The inflation pressure profile of the variable diameter inflation balloon 18 illustrated in Table 2 provides an example of the manner in which a balloon 18 made in accordance with the foregoing method is inflated with the application of increased pressure. Initially, the central segment 30 and the proximal and distal segments 26, 28 of the balloon 18 inflate together in vitro as the pressure increases. When the pressure reaches 6 ATM, for example, the diameter of the proximal and distal segments 26, 28 and the central segment 30 of the balloon all remain at about 2.5 mm. At 11 ATM, the diameter of the central segment 30 of the balloon 18 has grown to about 3 mm while the proximal and distal segments 26, 28 remained inflated to the first diameter of approximately 2.5 mm. The diameter of the central section 30 of the balloon 18 will continue to increase at least in vitro until the burst pressure of the balloon 18 is reached. In one prototype, the burst pressure was approximately 20 ATM at normal body temperature.

Both the first inflation diameter and the second inflation diameter can also be varied depending upon the desired catheter characteristics as will be understood by one of ordinary skill in the art. In a preferred embodiment, a first inflated diameter of the catheter for coronary angioplasty applications is approximately 2.5 mm. Upon an increase of pressure, this diameter grows to a second inflated diameter of approximately 3 mm in the central focal segment 30. In general, balloons can be readily constructed having a difference between the first inflation diameter and second inflation diameter anywhere within the range of from about 0.1 mm up to 1.0 mm or more, depending upon the elastic limits of the material from which the balloon was constructed. Typically, coronary angioplasty dilatation balloons will have a first diameter within the range of from about 1.5 mm to about 4.0 mm. Typical balloons for use in peripheral vascular applications will have a first inflation diameter within the range of from about 2 mm to about 10 mm.

Dilatation balloons can readily be constructed in accordance with the present invention in which entire length of the balloon from, for example, proximal shoulder 42 to distal shoulder 46 (FIG. 2) is variable from a first inflated diameter to a second larger inflated diameter in response to increasing pressure. Alternatively, balloons in accordance with the present invention can readily be constructed in which a proximal portion of the balloon is compliant so that it can grow in response to increased pressure, while a distal portion of the balloon has a fixed inflated diameter. This configuration may be desirable, for example, when the native vessel diameter is decreasing in the distal catheter direction. Positioning the catheter so that the compliant portion is on the proximal (larger diameter) portion of the vessel may minimize damage to the vessel wall in certain applications. Alternatively, the compliant segment can readily be positioned on the distal end of the balloon with a substantially fixed inflated diameter segment on the proximal end of the balloon.

A variable diameter balloon 18 made in accordance with the foregoing designs has been found to benefit certain conventional percutaneous transluminal coronary angioplasty (PTCA) procedures. In accordance with the method of the present invention, the variable diameter balloon 18 is percutaneously advanced and positioned such that the central segment 30 of the balloon 18 is adjacent a vascular treatment site. Generally, the treatment site is a stenosis such as due to a plaque or thrombus. The variable diameter balloon 18 is inflated to a first inflation profile to begin dilation of the stenosis. Preferably, the first inflation profile is achieved by applying up to about 6 ATM of pressure to the balloon 18. At the first inflation profile, the entire balloon is inflated to the inner diameter of the vessel, thus restoring patency to the vascular lumen. In one embodiment, the variable diameter balloon 18 is inflated to a first inflation diameter, of about 2.5 mm, at an inflation pressure of 6 ATM. The first inflation diameter is preferably about the native diameter of the vessel.

As additional pressure is applied to the variable diameter balloon 18, a second inflation profile is achieved wherein the central segment 30 of the balloon 18 expands beyond the diameter of the first inflation profile to a second inflation diameter, while the proximal segment 26 and the distal segment 28 remain at or substantially at the first inflation diameter. As the pressure applied to the variable diameter balloon 18 increases, the diameter of the central segment 30 of the balloon 18 extends past the native diameter of the vessel to the second inflation diameter. Utilizing this method, and depending upon the balloon size selected, the stenosis is compressed to a point which is beyond the native diameter of the vessel. In a preferred embodiment, at an applied pressure of 11 ATM the diameter of the central segment 30 of the balloon 18 at the second inflation diameter is 3 mm and the diameter of the proximal end 26 and the distal end 28 at the first inflation diameter is approximately 2.5 mm. Second inflation diameters in between the first inflation diameter and the maximum inflation diameter can be readily achieved by controlling inflation pressure, as illustrated for one embodiment in Table 2, above.

After the stenosis is compressed to or beyond the native diameter of the vessel, the balloon is evacuated and the catheter withdrawn. Alternatively, if desired, the pressure is reduced until the balloon 18 resumes the first inflation profile. At this point, the balloon 18 may be held at the first inflation diameter for short periods to continue to maintain patency of the lumen if short term rebound is a concern. This post dilatation step is preferably accomplished using a catheter having perfusion capabilities. Finally, the remaining pressure applied to the balloon 18 is reduced causing the variable diameter balloon 18 to deflate. The catheter is then extracted from the vessel utilizing conventional PTCA procedures.

The "focal" or "differential compliance" balloon of the present invention provides important real time diagnostic information about the lesion being treated. In a balloon having one or more noncompliant or substantially noncompliant zones such as proximal segment 26 and distal segment 28 and a central focal segment 30, (FIG. 2) inflation within a lesion will proceed through a series of discreet phases. The phases can be visually differentiated by observing the balloon fluoroscopically and comparing the apparent diameter of the central section with the diameter of the one or more substantially noncompliant zones. The substantially noncompliant zones may be considered reference zones for present purposes.

When the balloon 18 is inflated within a lesion, the reference zone will normally be positioned proximally or distally of the lesion and the central zone will be centered within the lesion. As balloon inflation begins, the overall balloon may take on a "dog bone" shape with the central portion radially inwardly restrained by the lesion. As inflation pressure is increased, the central section will tend to expand until the balloon has assumed an overall generally cylindrical profile. At a certain higher pressure, the balloon will focalize, such that the central region has reached its second, larger inflated diameter. By observing the first pressure at which the balloon assumes a generally cylindrical configuration and the second higher pressure at which the balloon focalizes, the clinician can learn important information about the morphology of the lesion.

For example, in a balloon rated 3.0 mm at 6 atmospheres, the reference zone may grow to 3.2 mm at 11 atmospheres. The focal section will grow to 3.0 mm at 6 atmospheres, and, in a healthy artery, should grow to 3.5 mm at 11 atmospheres. If there has been no focalization at 11 atmospheres, the clinician will know that the lesion is highly calcified or is otherwise highly resistant to expansion. The pressure can then be gradually increased up to a maximum pressure which approaches the burst pressure, and the pressure at which focalization is finally visualized will reveal information about the degree of calcification or other information about the lesion.

Thus, there is provided in accordance with the present invention a method of obtaining characterizing information about a lesion. The characterizing information is obtained by positioning a differential compliance balloon in the artery such that a central focal section is positioned within the lesion. The balloon is inflated to a first inflation pressure such that the balloon achieves a "dogbone" configuration with the lesion. The clinician preferably notes that first pressure. The pressure is increased until the balloon achieves a generally cylindrical exterior configuration. The pressure at which the substantially cylindrical configuration is achieved is preferably noted. The pressure in the balloon is increased further until focalization of the central section is achieved, and the focalization pressure is noted. One or more of the noted pressures may be compared to other information concerning the same patient or against reference data to assess the nature of the lesion. Since the balloon can be readily fluoroscopically visualized, the clinician receives real time information about the size of the inflation balloon merely by visually comparing the focal section with the reference section. If, at a particular pressure, the balloon is "straight across" (i.e. has not focalized) the clinician can look at the reference chart for the balloon or rely upon experience to assess the diameter of the vessel at the treatment site.

In accordance with another aspect of the present invention, there is provided a method of interactive angioplasty using the differential compliance balloon of the present invention. In general, the interactive angioplasty method involves inflating the balloon to a first inflation pressure, which should produce a first inflation profile for a particular expected lesion morphology. If the profile of the balloon at the first inflation pressure is different than the expected first inflation profile, the clinician will know that the lesion morphology may be different than anticipated. The clinician can thus responsively change the course of treatment, such as by removing the catheter and replacing it with a different one.

For example, if a highly calcified or fibrotic lesion is expected and the first inflation pressure produces a substantially cylindrical balloon rather than a dogbone shaped balloon, the clinician may determine that the balloon selected was too small or the lesion was not calcified or fibrotic as expected. That balloon catheter may be withdrawn and a catheter having a larger balloon thereafter positioned in the lesion. If the expected degree of inflation at the focal zone (compared, for example, to the reference zone) fails to occur at the expected inflation pressure, the clinician may alternatively elect to increase the inflation pressure, thereby exerting a greater force on the lesion.

Alternatively, lesion morphology information obtained by comparing the expected inflation profile at a given pressure stage with the actual inflation profile may cause the clinician to seek alternate treatment, such as drug therapy, surgery, or other techniques that may be available at the time. More rapid progression than expected from dogbone to cylindrical to focalized inflation may indicate the presence of soft placque or of a thrombosis, and measures can be taken in response to minimize the risk of over dilatation or embolization. These measures may include drug therapy such as local administration of streptokinase or TPA, or other measures such as atherectomy, laser therapy or stenting.

One of the advantages of the interactive angioplasty of the present invention is that the clinician can alter the course of treatment during the procedure, in response to information obtained during the procedure about lesion morphology or progression of the procedure. For example, if the balloon fails to focalize at the pressure previously expected to produce focalization, depending upon other circumstances of the patient, the clinician may determine that further dilatation of the lesion will produce an undesirable dissection of the artery, and a different treatment may be indicated. Alternatively, the clinician may elect to simply increase the inflation pressure until focalization occurs, or substitute a different balloon having a different inflation diameter or capable of sustaining a greater inflation pressure.

At each of the reference points identified previously herein, such as the dogbone profile, the cylindrical profile, and the focalized profile, any deviation from the expected pressure to achieve that profile can thus be noted by the clinician and used to assess the course of further treatment. The interactive angioplasty method of the present invention can be accomplished both in the context of balloon dilatation and also in the context of implantation and or sizing of an intervascular prosthesis (stent).

Figure 5:
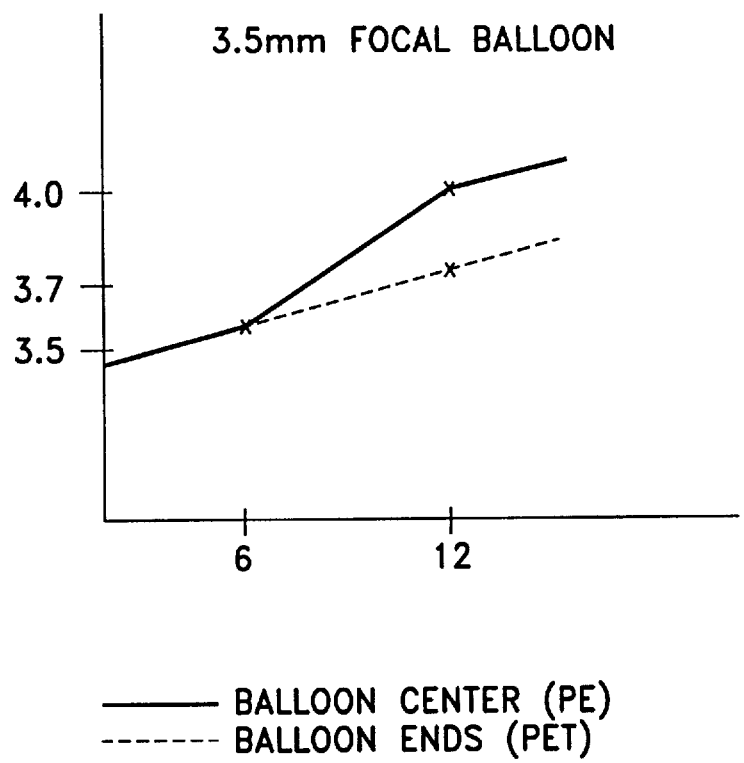
FIG. 5 illustrates a comparison of compliance curves between the reference zones and the focal zone as a function of increased inflation pressure in a differential compliance focal balloon of the present invention.

Pressure response data for a series of exemplary balloons manufactured in accordance with the present invention using techniques described previously herein is provided in Table III below. The compliance curves for a reference zone and a focal zone of a differential compliance balloon rated for 3.5 mm at 6 atmospheres are illustrated in FIG. 5.

TABLE III

EFFECT OF INCREASED PRESSURE ON BALLOON DIAMETER

| Balloon | 11 ATM | 14 ATM | 16 ATM |
| --- | --- | --- | --- |
| 3.0 mm | | | |
| Reference Zone | 3.2 mm | 3.2 mm | 3.3 mm |
| Focal Zone | 3.5 mm | 3.5 mm | 3.5–3.7 mm |
| 3.5 mm | | | |
| Reference Zone | 3.7 mm | 3.7 mm | 3.8 mm |
| Focal Zone | 4.0 mm | 4.0 mm | 4.0–4.2 mm |
| 4.0 mm | | | |
| Reference Zone | 4.2 mm | 4.2 mm | 4.3 mm |
| Focal Zone | 4.5 mm | 4.5 mm | 4.5–4.7 mm |

As exemplified in Table III, the reference zones on a particular balloon are expected to have a predetermined diameter at certain pressures. For example, the reference zones on a 3.0 mm balloon are expected to inflate to 3.2 mm at 11 ATM. If the balloon appears to be "straight across" at 11 ATM, the clinician knows that the focal section and therefore the lesion has been inflated to 3.2 mm. If the balloon has focalized, the clinician knows that the lesion has been inflated to 3.5 mm by referring to a look up table containing the balloon specifications. If focalization does not occur until a higher pressure such as 14 ATM has been reached, the clinician still knows that the lesion has been inflated to 3.5 mm, but also knows that the lesion was relatively calcified or fibrotic.

The present interactive angioplasty invention thus enables the clinician to take into account the difference in balloon inflation characteristics between the in vitro and in vivo environments. Balloons in vitro exhibit a predictable inflation response to pressure. Balloon inflation in vivo, however, can be quite different from the balloon rating, and also from lesion to lesion, as a result of the differences in vessel wall thickness, lesion morphology and other characteristics that affect the resistance to radial expansion in the area of the target lesion. By providing reference information such as the inflated diameter of the reference and focal zones of a balloon at each of a series of pressures, the clinician can determine the actual diameter of the balloon in the focal zone by observing the balloon in either of the "straight across" or focalized inflation profiles.

The differential compliance balloon of the present invention is also particularly suited for the implantation and or sizing of intravascular stents. For example, in a 3.2 mm vessel, it may be desirable to dilate a stent to 3.5 mm inside diameter since some stents tend to recoil in vivo. If the balloon is inflated up to 10 ATM with no focalization, the clinician knows to increase the pressure until a focal section becomes apparent. When the focal section has become apparent, the clinician will know that the inside diameter of the stent has been appropriately inflated to 3.5 mm.

In accordance with a further aspect of the present invention, there is provided a method of implanting a tubular stent within a body lumen. Tubular stents of the type adapted to be carried to a vascular site on a balloon catheter, and for expansion from a first insertion diameter to a second implanted diameter are well-known in the art.

In accordance with the method of implanting a tubular stent, an expandable stent is positioned about the deflated balloon of a variable diameter balloon catheter in accordance with the present invention. The balloon is thereafter percutaneously inserted into the vascular system and transluminally advanced to position the stent at the treatment site. The balloon is thereafter inflated to at least a first inflation configuration, wherein the balloon exhibits a substantially cylindrical profile throughout its axial length. Thereafter, the balloon is optionally inflated to a second inflation profile, thereby inflating at least a portion of the stent to a second, greater diameter. Depending upon the etiology of the underlying condition, the central region of the stent may preferentially be inflated to a larger diameter than either of the axial ends of the stent. Alternatively, the axial length of the stent is selected to approximately equal the axial length of the focal zone on the inflation balloon. In this manner, the inflation balloon within the stent is expandable to a diameter slightly larger than the native diameter of the adjacent vessel. This permits subsequent overgrowth of endothelium along the interior wall of the stent while still leaving a lumen having an interior diameter within the stent approximately equal to the native diameter of the lumen adjacent the stent.

In accordance with a further aspect of the present invention, the variable diameter balloon is utilized to "tack down" a previously positioned tubular stent. In accordance with this aspect of the present invention, a tubular stent is identified within a body lumen. The focal balloon is positioned within the stent in accordance with conventional PTCA procedures, and the balloon is inflated so that the central, focal section enlarges the diameter of at least a first portion of the stent. The balloon is thereafter reduced in diameter, and, preferably, repositioned within a second region within the stent and then reinflated to expand at least the second region of the stent. Expansions of this type can be repeated until the stent has been expanded as desired. The balloon is thereafter evacuated and removed from the patient.

In accordance with a further aspect of the present invention, there is provided a method of percutaneous transluminal angioplasty in which multiple lesions of differing sizes are dilated without removing the catheter from the body. In accordance with this aspect of the present invention, the variable diameter balloon is positioned within a first stenosis in accordance with conventional PTCA techniques. The balloon is dilated to a sufficient diameter to restore patency to the vascular lumen. The balloon is thereafter deflated, and repositioned within a second stenosis in the vascular system. The balloon is inflated to restore patency of the vessel in the region of the second stenosis. Optionally, the balloon may be deflated, and repositioned within a third stenosis in the body lumen. The balloon is then inflated to a sufficient diameter to restore patency in the body lumen in the region of the third stenosis. Four or more lesions can be treated seriatim in this manner.

Preferably, the balloon is inflated to a first diameter in the first stenosis, and to a second, different diameter, in the second stenosis. In this manner, multiple dilatations at different diameters can be accomplished utilizing the balloon of the present invention. This method is accomplished by supplying a first inflation pressure to the balloon while the balloon is positioned in a first position in the vascular system, and thereafter supplying a second pressure to the balloon when the balloon is in a second position in the vascular system. In accordance with the previous disclosure herein, each of the first and second inflation pressures is selected to achieve a preselected inflation diameter of the balloon.

Figure 7:
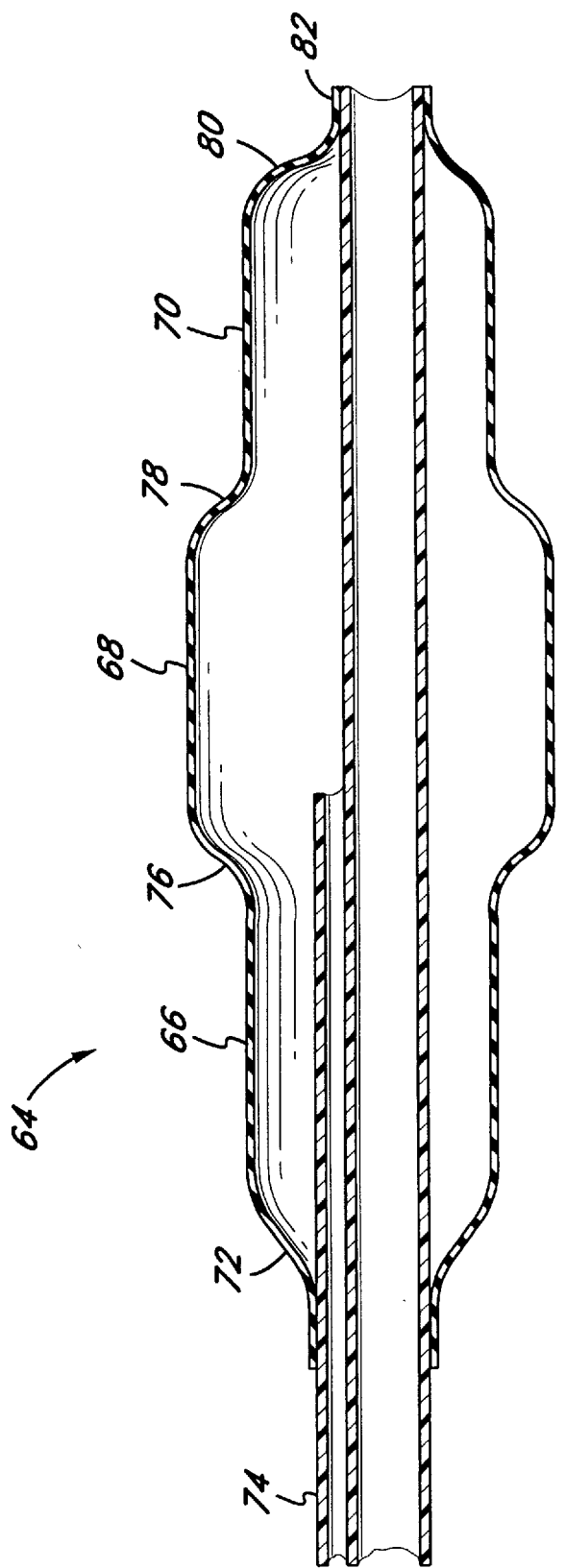
FIG. 7 is a cross sectional schematic illustration of a fixed focal balloon catheter of the present invention.

A number of the advantages of the interactive angioplasty methods and stent implantation and sizing methods of the present invention can also be accrued through the use of an alternate embodiment of the balloon of the present invention as illustrated in FIG. 7. Referring to FIG. 7, there is disclosed a fixed focal balloon 64. By "fixed" focal balloon, it is meant that the balloon assumes a stepped configuration in its initial in vitro inflated profile. Increased inflation pressure beyond the pressure necessary to achieve the initial stepped inflation profile does not appreciably change the relative proportionality of the profile from its initial stepped configuration.

The stepped configuration is characterized by a difference in diameter between at least one reference zone and a focal zone, preferably on the same balloon. The fixed focal balloon of the present invention can be constructed using either relatively compliant or relatively noncompliant materials, with the resulting characteristics that will be readily apparent to those of skill in the art in view of the disclosure herein. Preferably, the fixed focal balloon comprises polyethylene terephthalate.

The embodiment of the fixed focal balloon 64 illustrated in FIG. 7 has a central focal zone and a proximal as well as a distal reference zone. However, the present inventors also contemplate fixed focal balloons in which either the proximal reference zone or the distal reference zone is omitted. These embodiments include only a single reference zone and a single focal zone. The reference zone may be positioned either proximally or distally of the focal zone.

For example, in one two segment embodiment of the present invention, a proximal segment on the balloon is inflatable to a greater diameter than a distal segment. In general, the proximal segment will inflate to a generally cylindrical configuration in an unconstrained inflation. A transition zone is disposed at the distal end of the proximal segment. In the transition zone, the diameter of the balloon steps down to the smaller inflated diameter of the distal segment. The axial lengths and diameters of the proximal and distal segments can vary widely depending upon the intended use of the balloon. In one application, the balloon is used to size or implant two stents positioned end to end in a vessel. The stents may comprise a pair of 15 mm length stents or 20 mm length stents or otherwise as may be desired. For this application, the balloon may have an overall length of from about 20 mm or 30 mm to about 40 mm or greater. In one 30 mm balloon, a proximal segment is approximately 15 mm long and has an inflated diameter of about 3.5 mm. At the distal end of the proximal segment is a transition zone which will be generally be less than 1 or 2 mm in length and preferably about a ½ mm in length. Distally of the transition zone is a second segment approximately 15 mm in length and having an inflated diameter of about 3.0 mm. Alternate pairs of proximal and distal segment inflated diameters may also be utilized as will be appreciated by those of skill in the art. In general, the difference in diameter between the proximal and distal segments will be within the range of from about 0.2 mm to about 1 mm, and, preferably, will be about 0.5 mm. Proximal and distal segment diameter and pairs for balloons believed useful by the present inventor include 4.0/3.5 mm, 3.5/3.0 mm, 3.0/2.5 mm. Proximal and distal balloon zone lengths are preferably approximately equal in a given balloon, e.g., 20 mm/20 mm in a 40 mm balloon, although dissimilar zone lengths may be desirable in particular specialty applications.

As a further alternative, the balloon is provided with three stepped diameters in the inflated profile. In a 30 mm balloon, for example, a proximal 10 mm section inflates to a first diameter, an intermediate 10 mm section inflates to a second diameter and a third 10 mm section inflates to a third diameter. Preferably, the first, second and third diameters decrease in the distal direction. The diameters of adjacent sections may be separated by 0.5 mm, 0.25 mm, or other differential as may desired for the intended application. Thus, in an exemplary balloon, the first diameter is 3.5 mm, the second diameter is 3.0 mm and the third diameter is 2.5 mm. In an alternate example, the first diameter is 3.5 mm, the second diameter is 3.25 mm and the third diameter is 3.0 mm. Similar gradations from about 2 mm up through about 4.5 mm for coronary applications, and up to 8 or more millimeters for other applications may be used.

Any of the preceding multizone balloons, particularly the two zone and three zone balloons can be utilized to implant or size a single "long" stent or expandable graft. For present purposes, long stents will have an axial length of greater than about 20 mm, and could have any of a variety of lengths such as 25, 30, 35, 40, 45, 50, 55, 60 mm or longer. Corresponding balloon lengths are also contemplated. Stent and balloon lengths intermediate the foregoing dimensions may also be utilized, as will be appreciated by those of skill in the art. Two or three or four or more axially adjacent stents may also be implanted or sized using the catheters described herein.

Any of the balloon catheter designs described herein may be utilized in the method of implanting a tubular stent, the method of sizing a previously implanted stent, or simultaneously implanting and sizing tubular stents (which term is intended to include grafts throughout). The balloon catheters disclosed herein are also useful in the methods of simultaneously implanting and/or sizing multiple stents.

Alternatively, the proximal and distal zones in a three zone balloon may be inflatable to the relatively larger diameter, while the central zone is inflated to the smaller, reference diameter. This embodiment may be considered to have a proximal and a distal focal zone and a single central reference zone. These and additional variations are illustrated in FIGS. 8–18, discussed infra. The desirability of one combination over another will be governed by the requirements for a particular balloon dilatation or stent or graft implantation procedure as will be apparent to those of skill in the art in view of the disclosure herein.

Referring to the embodiment illustrated in FIG. 7, the fixed focal balloon 64 is provided with a proximal reference zone 66, a central focal zone 68 and a distal reference zone 70. The relative lengths of each of these zones may vary considerably depending upon the intended use of the balloon. In general, any of the dimensions of the balloon, both in terms of diameters and lengths as well as other catheter dimensions, may be the same as those disclosed in connection with other embodiments previously disclosed herein. In one particular application, the focal zone 68 has an axial length of 10 millimeters, and each of the proximal zone 66 and distal zone 70 has an axial length of about 5 millimeters. At 8 atmospheres inflation pressure, the proximal reference zone 66 has an outside diameter of about 3 millimeters, and the focal zone 68 has an outside diameter of about 3.4 millimeters. The same balloon at 18 atmospheres inflation pressure has an outside diameter of about 3.1 millimeters in the proximal reference zone 66 and an outside diameter of about 3.5 millimeters in the focal zone 68. That particular balloon was constructed from PET, having a wall thickness of about 0.0006–0.0008 inches.

Depending upon the desired clinical performance of the balloon, the relative expansion characteristics of the reference zone compared to the focal zone can be varied. For example, although the focal section will normally retain a larger inflated diameter than the reference zone, the reference zone may grow in response to an increase in inflation pressure a greater amount than the focal zone. In one PET balloon, having a wall thickness in the range of from about 0.0006 to about 0.0008 inches, the growth of the reference zone upon an increase in inflation pressure from 8 to 18 atmospheres was about 0.2610 millimeters. The growth in the focal zone over the same pressure increase was about 0.1457 millimeters. It may alternatively be desired to achieve a greater growth in the focal zone compared to the reference zone, or an equal growth in each zone as a function of increased pressure. Optimizing the growth response to increased pressure of the focal zone relative to the reference zone for any particular intended application can be accomplished by the exercise of routine skill in the art in view of the disclosure therein.

The fixed focal balloon 64 further comprises a first transition 72 which steps the diameter of the balloon up from the diameter of the catheter shaft 74 to the diameter of the proximal reference zone 66. All balloons have some form of transition, such as first transition 72, and the reference zone 66 is to be distinguished from what is simply a transition, such as transition 72. Thus, the reference zone 66 is provided with a visibly discernable generally cylindrical exterior configuration in the inflated state, or other characteristic inflated configuration, so that it can be distinguished visibly from the transition 72 in vivo. Thus, the proximal reference zone 66 can be either a cylindrical section which transitions sharply into a generally conical transition section, such as first transition 72. Alternatively, the reference zone 66 may comprise a continuation of a first transition 72, but with a visibly different angle with respect to the longitudinal axis of the catheter when compared to the angle of the surface of the first transition 72 taken in the axial direction. In one embodiment of the invention, the surface of the first transition 72 measured in the axial direction lies at an angle of approximately 20 degrees with respect to the longitudinal axis of the catheter shaft 74.

A second transition 76 is provided to step the diameter of the inflated balloon from that of the proximal reference zone 66 to the focal zone 68. A third transition 78 is provided to step the outside diameter of the inflated balloon from the diameter of focal zone 68 down to the diameter of distal reference zone 70. The angle of each of the second and third transition sections can vary depending upon desired performance and design characteristics, but in one embodiment of the invention have a surface which lies on a plane extending in the axial direction at an angle of about 11° from the longitudinal axis of the catheter shaft 74. The axial length of each of the second transition 76 and third transition 78 will vary depending upon the difference in diameter of the focal zone from the reference zone, but will generally be within the range of from about 0.5 mm to about 4 mm.

A fourth transition 80 is provided to step the diameter of the balloon 64 from that of the distal reference zone 70 back down to the diameter of the distal catheter shaft or tip 82.

The three zone embodiment illustrated in FIG. 7 can be produced having any of a variety of dimensions, depending upon the particular contemplated end use of the catheter. In the following nonlimiting examples of balloon dimensions, the dimensions for the balloon are recited at 8 atmospheres inflation pressure in an unrestrained (in vitro) expansion.

For example, balloons can be readily provided having a focal zone 68 inflatable to an initial inflation diameter of anywhere within the range from about 1.5 mm to about 10 mm. For coronary vascular applications, the focal zone will normally be inflatable to a diameter within the range from about 1.5 mm to about 4 mm, with balloons available at every 0.25 mm increment in between.

The reference zone, such as proximal reference zone 66 and/or distal reference zone 70 is preferably inflatable to a diameter within the range from about 1.25 mm to about 9.5 mm. For coronary vascular applications, the reference zone is preferably inflatable to a diameter within the range of from about 1.25 mm to about 3.5 mm.

The focal zone is normally inflatable to a generally cylindrical profile, which has a diameter that is greater than the diameter in the reference zone. Neither the focal zone nor the reference zone or zones need to be precisely cylindrical. Thus, the present invention can still be accomplished with some slight curvature or bowing of the surface of the focal zone or reference zone taken along the axial direction.

In general, the maximum diameter of the focal zone will be within the range of from about 7% to about 30% percent or more greater than the average diameter of the reference zone. Preferably, the maximum diameter in the focal zone will be at least about 10% greater than the average diameter in the reference zone.

The configuration of the reference zone compared to the focal zone can be varied considerably, as long as the reference zone and the focal zone outer diameters can be visualized by the clinician using conventional fluoroscopic or other visualization techniques. Thus, although the reference zone can take on a slightly conical configuration such that it ramps radially outwardly in the direction of the focal zone, it should not be to such an extent that the clinician cannot visually differentiate the inflation profile of the focal zone compared to the reference zone in vivo.

The function of the reference zone, to provide a visual reference to indicate the relative inflation of the focal zone, can be accomplished by the provision of radio opaque markers at either end of or within the balloon. For example, inflatable or flexible radio opaque markers may be provided along the transition in a balloon from the catheter shaft to the working zone in an appropriate position along the ramp such that, when the balloon is inflated, the radio opaque marker provides a visual indication of a predetermined diameter. Alternatively, the use of radiopaque inflation media to inflate the balloon can also permit in vivo visualization.

Although the preferred embodiments described above rely upon the balloon to provide a visual reference, the objectives of the present invention may be accomplished using other visual indicia which will permit the clinician to assess the relative in vivo inflation of the focal zone. Thus, in a broad sense, the invention contemplates a visualizable aspect associated with the focal section and a visualizable reference indicia such as the balloon, a radiopaque marker on or associated with the balloon, radiopaque inflation media, or others, which allows the clinician to compare the diameter of the focal section relative to some other visual reference.

In addition to the provision of a visual reference to allow the clinician to assess the inflated diameter of the balloon, the balloon of the present invention provides a way to focalize the balloon inflation energy at a predetermined position along the balloon. The axial length of the focal section can be varied considerably, depending upon the desired axial length along which inflation energy is to be focalized. For example, the axial length of the focal section may be anywhere within the range of from about 0.5 cm to about 5.0 cm. For coronary vascular applications, the axial length of the focal balloon will normally be within the range of from about 0.5 cm to about 2.0 cm for performing conventional PTCA. The axial length will normally be within the range of from about 0.5 cm to about 5 cm for implanting expandable tubular stents, depending upon the length of the desired stent. Normally, the axial length of the focal section will be greater than the axial length of the stent.

A variety of focal balloon catheters of the present invention are preferably available to the clinician having an array of different axial focal lengths, so that a balloon having the appropriate focal length can be selected at the time of the procedure based upon the nature of the procedure to be performed, and the location in the vasculature. For example, in a curved portion of the artery, the clinician may wish to minimize the axial length of the focal zone to the extent possible while still having a sufficient axial length to accomplish the dilatation or stent implantation procedure. An excessive axial length in the inflated balloon for a given curved vessel can elevate the risk of vascular dissection as is well known in the art.

The axial length of the reference zone can also be varied considerably, depending upon the desired performance characteristics. In general, it has been found that axial lengths of at least about 3 mm allow ready visualization by the clinician. Axial lengths much shorter than 3.0 mm may require too much effort to observe under fluoroscopic conditions, and the reference function of the reference zone may thus not be readily accomplished.

In one embodiment of the invention, produced in accordance with the three-zone illustration of FIG. 7, the proximal and distal reference zones each have an axial length of about 5.0 mm and an inflated diameter of about 3.0 mm at 8 ATM. The axial length of the focal zone, including the length of the second transition 76 and third transition 78, is about 8 mm. The diameter of the focal zone at 8 atmospheres inflation pressure is about 3.5 mm.

The fixed focal balloon 64 can be manufactured using any of a variety of techniques which will be understood to those of skill in the art. For example, the balloon can be manufactured by blowing suitable tubing stock into a stepped mold cavity. Alternatively, the tubing stock can be blown into a first mold having a diameter approximately equivalent to the reference diameter. The balloon can then be blown into a second mold having a larger diameter section corresponding to the focal section in the finished balloon. The balloon is inflated into the larger mold under the application of heat, as will be understood by those of skill in the art.

The fixed focal balloon 64 of the present invention or other fixed focal balloons as described herein can be utilized in any of the methods described in connection with the differential compliance balloons of the present invention. Thus, the real-time diagnostic information about the lesion which is obtainable through the use of the focal or differential compliance balloons described in connection with FIGS. 1–6 herein can also generally be achieved using the embodiment of FIG. 7. Unless clearly specified to the contrary, the various methods of the present invention, including both the differential compliance and stent implantation and sizing methods, are intended to be accomplished by either the fixed focal balloon or the variable focal balloon embodiments of the methods of the present invention.

FIGS. 8–18 illustrate a variety of specialized focal and/or compliant zone balloons in accordance with the present invention. These balloons can incorporate any of the structures, features, and methods of the previous embodiments as may be desirable for particular intended applications. Therefore, construction techniques, materials, dimensions, capabilities and methodology discussed above applies to the following embodiments, but will generally not be repeated below.

An alternate multi-zone balloon design of the present invention is schematically illustrated in FIGS. 8 and 9. Referring to FIG. 8, there is disclosed a catheter having an elongate flexible tubular shaft 84 such as has been discussed in connection with previous embodiments. The catheter shaft 84 is provided with a guidewire lumen 85 and at least one inflation lumen 86. Guidewire lumen 85 terminates in a distal opening 87 at the distal end 88 of the catheter.

A distal region on the catheter is provided with a balloon assembly 89. The balloon assembly 89 comprises an inner inflatable balloon 90 disposed within an outer inflatable balloon 91. Inflation lumen 86 provides fluid communication between a proximal source of inflation media (not shown) and the interior of the inner balloon 90. The construction materials, construction techniques and dimensions of the various components of the various balloons and catheters illustrated in FIGS. 8 through 18 can be the same or similar to as those disclosed in connection with previous embodiments. For example, the inner balloon 90 may be constructed from a relatively noncompliant material such as PET or a relatively compliant material such as polyethylene.

The balloon assembly 89 is configured to produce a three zone balloon of the type that has been previously discussed, such that the balloon assembly 89 is inflatable first to a generally cylindrical configuration as illustrated in FIG. 8 and, thereafter, to a stepped configuration such as that illustrated in FIG. 9. Thus, a focal zone 92 (also referred to herein as a compliant zone) is disposed adjacent one or more reference zones, such as proximal reference zone 93 and distal reference zone 94.

In this embodiment, the inner balloon 90 and outer balloon 91 are designed to substantially maintain contact with each other, except in the region of the focal section 92 once that section has focalized. Inner balloon 90 and outer balloon 91 may be maintained in contact at their proximal and distal ends such as by the use of thermal bonding, adhesives, or other techniques described elsewhere herein. In addition, expansion limiting bands as have been previously discussed may also be incorporated into the balloons illustrated in FIGS. 8 and 9, such as in the reference zones 93 and 94.

One feature which distinguishes the balloon illustrated in FIGS. 8 and 9 from those previously discussed is the provision of one or more apertures 95 for providing communication between the interior 96 of balloon 90 and the interior 97 of outer balloon 91. Apertures 95 permit a rate controlled diffusion of inflation media from the interior 96 of balloon 90 into the space 97 to provide a delayed, gradual focalization of the focal section 92. In use, the foregoing features permit the clinician to inflate the balloon assembly 89 to a preselected pressure, which will cause the balloon assembly 89 to inflate to its generally cylindrical inflation profile. Migration of inflation media through the ports 95 then cause the compliant section 92 to gradually inflate to the second, stepped configuration of the balloon assembly as illustrated in FIG. 9.

Preferably, a plurality of discrete ports 95 is provided in the balloon 90 to enable the diffusion of inflation media at a desired rate into the focal section 92. The ports 95 are preferably each within the range of from about 50 microns to about 400 microns across, and more preferably are within the range of from about 100 to about 300. In one embodiment, the ports are about 250 microns in diameter. Depending upon the desired rate of focalization, there are preferably anywhere from about 5 to about 50 inflation ports 95 on the inner balloon 90. Alternatively, a different number of ports and/or port diameters can be used depending upon the desired inflation characteristics of the balloon as a function of time. The number and size of the inflation ports 95 thus can be optimized for a particular desired inflation characteristic, taking into account the viscosity of the inflation media at the temperature the media is likely to be during an anticipated procedure.

In one embodiment, the outer balloon 91 comprises a relatively noncompliant material, which is preformed into the second, stepped configuration. In this embodiment, a relatively high pressure can be introduced into inner balloon 90. Inflation media will diffuse through ports 95 into the focal zone 92, thereby causing the balloon to assume its second, stepped configuration substantially without actual expansion of the material of the focal section 92. Alternatively, at least the focal zone 92 of the outer balloon 91 and preferably the entire balloon 91 comprises a relatively compliant material as has been discussed, so that the focal zone 92 grows by stretching in response to pressure as inflation media diffuses across inflation ports 95.

Figure 10:
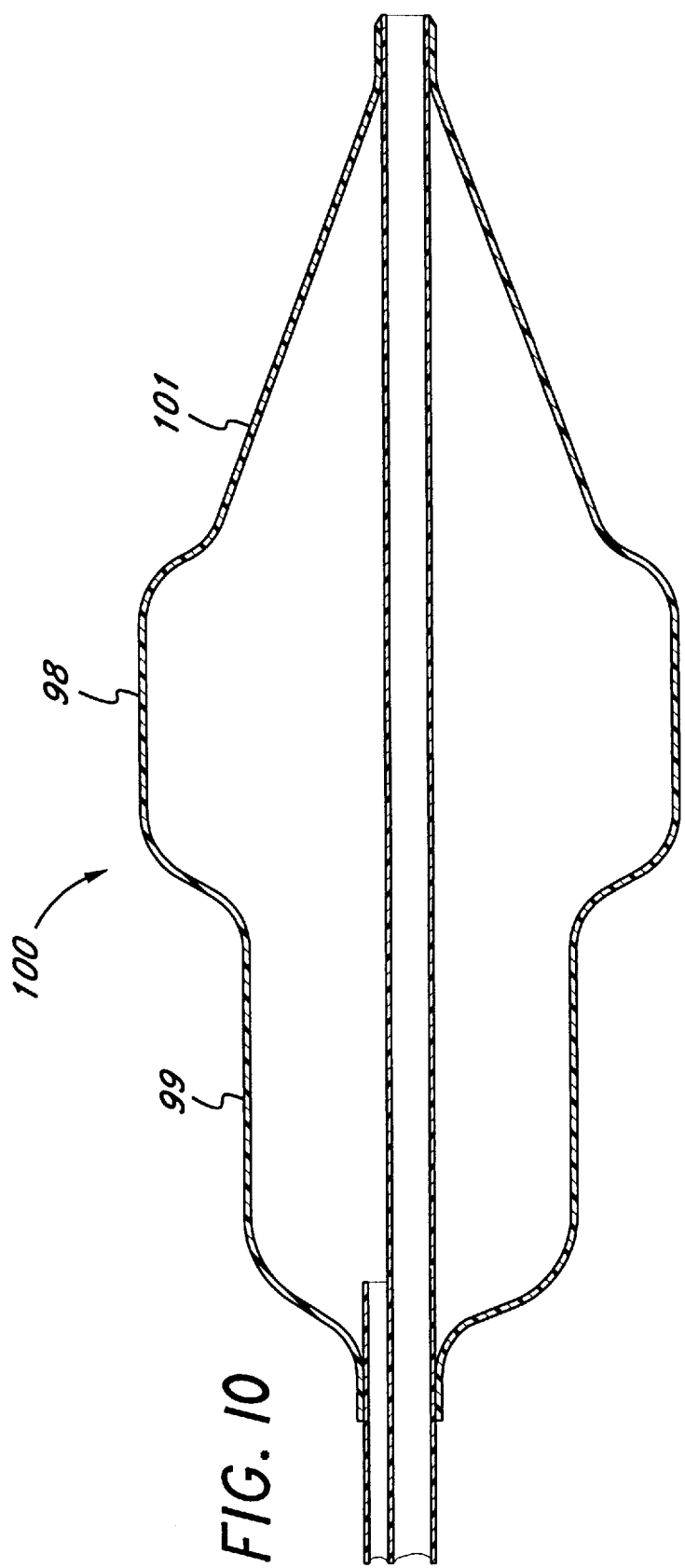
FIG. 10 is a cross sectional schematic view of a balloon profile having a focal zone and a tapered distal zone.

Referring to FIG. 10, there is illustrated a schematic outer profile of a distally tapered balloon 100 which may be utilized in connection with any of the embodiments disclosed elsewhere herein. In general, the outer profile comprises a focal zone 98, which may or may not be compliant. The focal zone 98 is adjacent at least one reference zone 99. In this embodiment, the reference zone 99 is disposed proximally of the focal zone 98. A distal section 101 is provided on the balloon distally of the focal section 98. Distal section 101 in the illustrated embodiment comprises an elongate tapered section which reduces in cross-sectional area in the distal direction. As an alternate embodiment, distal section 101 may comprise a generally cylindrical configuration, having a cross-sectional area in its inflated configuration which is smaller than the cross-sectional area of the proximal reference zone 99.

The above described modification to the exterior profile illustrated in FIG. 10 would thus produce a balloon having a configuration similar to that illustrated in FIG. 3. However, the distal cylindrical section or reference zone has a diameter which is less than the proximal cylindrical reference zone. In general, the inflated diameter of the distal reference zone will be no more than about 95% of the diameter of the proximal reference zone. Preferably, the inflated diameter of the distal reference zone will be no more than about 80% of the inflated diameter of the proximal reference zone. In one embodiment, the inflated diameter of the distal reference zone is about 3.0, the inflated focalized diameter of the focal section is about 3.5 and the inflated diameter of the proximal reference zone is about 3.25, at about 12 atmospheres.

Both of the foregoing modified distal segment configurations take into account the anatomical environment encountered during certain dilatations. For example, the native lumen in an artery on the catheter's distal side of the lesion is often smaller in diameter than the native lumen on the catheter's proximal side of the lesion. Provision of a distal section 101 having a step reduction or a tapered reduction in the inflated diameter can permit the catheter to accomplish all of the desired functions, while at the same time reducing the risk of dissection of the artery. In addition, the tapered distal section such as the embodiment illustrated in FIG. 8 may facilitate treatment of lesions or implantation of stents in or adjacent a curved segment of the artery, as will be apparent to those of skill in the art in view of the disclosure herein.

Referring to FIG. 11, there is disclosed a schematic illustration of a two inflation lumen catheter for use with certain embodiments of the balloons of the present invention. The catheter 102 comprises an inflatable balloon assembly 103 at its distal end as has been discussed. The catheter 102 is further provided with a manifold 104 having a guidewire access port 105 in an over the wire embodiment. As has been discussed, rapid exchange embodiments may also be constructed in which the proximal guidewire access port 105 is located along the length of the catheter shaft 102, such as in the area of about 20 or 25 centimeters proximally of the distal end of the catheter. In either embodiment, the distal end of the guidewire lumen typically exits the catheter at a distal port 106.

The manifold 104 in this embodiment is provided with a first inflation port 107 and a second inflation port 108 for communicating with a first inflation lumen 109 and a second inflation lumen 110, respectively.

Referring to FIG. 12, the first inflation lumen 109 is in fluid communication with the interior 112 of an inner balloon 114. The second inflation lumen 110 is in fluid communication with the potential space between the inner balloon 114 and an outer balloon 116. As has been previously discussed, inflation of the inner balloon 114 will in most embodiments cause the inner balloon 114 to assume a generally cylindrical inflated configuration. Inflation thereafter of the second balloon 116 will cause the second balloon 116 to assume a focalized configuration such as that illustrated in FIG. 13.

In an embodiment in which the outer balloon 116 is made from a relatively noncompliant material and preformed to have its stepped configuration, the outer balloon 116 need not necessarily be secured to the inner balloon 114. Thus, a small space may exist in the inflated configuration as illustrated in FIG. 13 between the outer balloon 116 and the inner balloon 114 in the proximal and distal segments. Alternatively, as has been discussed, the inner and outer balloons may be secured together in the proximal and distal zones, depending upon the desired balloon construction materials and performance characteristics.

In an embodiment where the inner balloon 114 and outer balloon 116 are secured together, a flow passage way 118 from the inflation lumen 110 to the focal section 120 can be readily provided such as by insertion of a mandril through the inflation lumen 110 and in between the balloons 114 and 116 prior to the method step of securing the balloon together. Proximal withdrawal of the mandril (not illustrated) will thereafter produce a flow passage way 118 as will be appreciated by those of skill in the art.

A variation of the embodiment of FIG. 13 is illustrated in FIG. 14. In this embodiment, a plurality of delivery ports 122 are illustrated in the focal section 120 of the outer balloon 116. Delivery ports 122 will facilitate the site specific delivery of substances to the vessel wall, such as drugs, or other diagnostic or therapeutic media as may be desired. This embodiment of the present invention may be constructed and utilized in a variety of manners similar to those disclosed in U.S. Pat. No. 5,421,826 to Crocker, et al., the disclosure of which is incorporated herein by reference.

As has been referenced, supra, a multizone balloon including the technology of the present invention may desirably include a proximal and a distal focal or compliant section, and a central reduced diameter section. Two embodiments of the present invention incorporating this feature are illustrated in FIGS. 15 and 16.

Referring to FIG. 15, there is disclosed a dual-lobed balloon catheter 130, comprising a single balloon 138 having a proximal lobe 140 and a distal lobe 142. By "single balloon" it is meant that the two or more lobes of the balloon may be inflated by way of a single inflation lumen. The actual balloon may comprise a single layer or a plurality of layers, depending upon the desired construction technique. For example, either one or each of the proximal lobe 140 and distal lobe 142 may have two or more layers, expansion limiting bands, or other structures as disclosed elsewhere herein. A central zone of reduced inflated diameter 144 is disposed between the proximal zone 140 and distal zone 142.

The balloon 138 is preferably mounted on an elongate flexible catheter shaft 132. Catheter shaft 132 is preferably provided with a guidewire lumen 134 and at least one additional lumen 136 such as for inflation of the balloon 138. Each of the proximal and distal lobes 140 and 142 may have any of the dimensions discussed in accordance with previous embodiments. In addition, either or both of the proximal and distal lobes 140 and 142 may comprise a compliant construction or a substantially noncompliant construction as has been discussed.

For example, balloon construction techniques disclosed previously herein can be utilized to produce a dual-lobed balloon 138 in which the proximal lobe 140 and distal lobe 140 inflate to a diameter of, e.g., about 2.5 millimeters at six atmospheres. As inflation pressure is increased to, for example, 14 atmospheres, either or both of the proximal and distal lobes may be restrained from expanding beyond about 2.6 or 2.7 millimeters. Alternatively, the proximal or the distal lobe 140 or 142 or both may expand to as much as about 3.3 millimeters or more at 14 atmospheres.

Selection of which of the proximal lobe 140 and distal lobe 142 to be expandable to a greater inflated diameter will depend upon the intended use of the catheter. For example, in most coronary vascular applications, the artery descends in diameter in the catheter distal direction. Thus, it may be desirable for the proximal lobe 140 to be inflatable to a larger final diameter. Alternatively, applications of the balloon catheter 130 for such things as drug or other media infusion, heart valve replacement or repair, or other uses will require different dimensional relationships between the proximal lobe 140 and distal lobe 142 as will be apparent to those of skill in the art in view of the disclosure herein.

The central zone 144 can have an inflated diameter anywhere within the range of from about the outside diameter of the catheter shaft to about 2.8 mm in a catheter for coronary vascular applications having a proximal balloon 140 with an inflated diameter of about three millimeters. The diameter of central section 144 may be constrained such as through the use of expansion limiting bands as has been discussed, or through the use of cross-linking techniques also discussed above. Alternatively, the central section 144 may be adhered to the catheter shaft 132, leaving only one or more axially extending flow paths for placing the interior of lobe 140 in fluid communication with the interior of lobe 142.

Referring to FIG. 16, the dual balloon counterpart to the design illustrated in FIG. 15 is disclosed. In general, dual balloon catheter 148 comprises a proximal balloon 150, a distal balloon 152 and a central zone 154 separating the proximal and distal balloons. The balloons are mounted on an elongate flexible catheter shaft 156. Catheter shaft 156 is provided with a guidewire lumen 158, together with at least a first and second inflation lumen 160 and 162. In the illustrated embodiment, inflation lumen 160 is in communication with proximal balloon 150 and inflation lumen 162 is in communication with distal balloon 152. In other respects, the discussion in connection with the dual-lobed balloon of FIG. 15 is applicable to the dual balloon embodiment of FIG. 16. In general, the dual balloon embodiment permits slightly more flexibility in terms of procedure, to the extent that it permits inflation of either the proximal or the distal balloon first, followed by inflation of the second balloon where clinically desirable.

Referring to FIGS. 17 and 18, there is disclosed a therapeutic or diagnostic agent delivery embodiment of the catheters illustrated in FIGS. 15 and 16. Referring to FIG. 17, there is illustrated a dual-lobed delivery balloon catheter 170. The catheter 170 comprises a dual-lobed balloon having a proximal lobe 172, a distal lobe 174 and a central neck portion 176. An outer perforated or permeable layer 178 extends at least from proximal lobe 172 to distal lobe 174 to entrap a space 180. Space 180 is preferably annular, and is in communication with an infusion lumen 182 by way of one or more flow pathways 184. In one embodiment, outer layer 178 comprises an elongate tubular sleeve, which is necked down at the proximal end of proximal lobe 172 and also at the distal end of distal lobe 174.

The diameter of neck portion 176 is preferably at least somewhat smaller than the diameter of proximal lobe 172 and distal lobe 174, to create space 180 for the accumulation of delivery media. A neck portion 176 which is inflatable to at least about 90% and preferably 95% or more of the diameter of adjacent lobes 172, 174 permits delivery of media through the delivery zone yet minimizes the entrapped volume within space 180. The inflated diameter of neck 176 can be limited by any of the inflation limiting techniques discussed above, such as one or more inflation limiting bands (not illustrated), cross linking, materials choice, wall thickness variations, and the like.

The inflated diameter of neck region 176 may alternatively be as small as permitted in view of the wall thickness of the balloon material, the wall thickness and diameter of the central guidewire lumen 184, plus the space attributable to at least one flow passage 186 for communicating between the proximal lobe 172 and distal lobe 174 of the balloon.

Outer layer 178 may comprise any of a variety of materials, such as compliant or noncompliant materials well known in the drug delivery and balloon dilatation arts. For example, layer 178 may comprise PET, polyethylene, or other membrane materials well known in the art. Layer 178 may be a permeable membrane, such that medication or other media diffuses therethrough. Alternatively, layer 178 is preferably provided with a plurality of perforations 188 for permitting media to escape from the annular chamber 180 to the surrounding area.

The diameter and distribution of the perforations 188 can be modified depending upon the objective of the catheter, such as will be understood by those of skill in the art in view of the disclosure herein. For example, provision of delivery perforations within the range of from about 100 microns to about 300 microns in diameter will permit a slow weeping expression of fluid media at low delivery pressures. Alternatively, reducing the cross-sectional area of the perforations and/or increasing the delivery pressure can permit the media to penetrate through the elastic lamina layer and into the arterial wall. Port 188 diameter and distribution characteristics should also be selected taking into account the viscosity of any media to be delivered, and/or particle size if a particulate media is to be delivered.

One advantage of the configuration illustrated in FIGS. 17 and 18 is the ability to isolate an arterial delivery zone in-between proximal lobe 172 and distal lobe 174. Inflation of the dual lobes within an artery can be accomplished at relatively low pressures to place the balloons in contact with the arterial wall. Infusion of media into annular chamber 180 for expression through ports 188 may then be accomplished. Inflation pressure on the balloon can be increased, if an undesirably large quantity of media escapes downstream.

FIG. 18 is in all respects similar to FIG. 17 except for the use of two separately inflatable balloons. The details and operation of FIG. 18 will be apparent to those of skill in the art in view of the discussions in connection with FIGS. 15–17.

Either of the drug delivery designs of FIGS. 17 and 18 may also incorporate a perfusion conduit, for permitting perfusion past the inflated balloon during a drug delivery period. Perfusion conduits such as those disclosed in U.S. Pat. No. 5,344,402 to Crocker, the disclosure of which is incorporated herein by reference, can be utilized.

Any of the hourglass type balloons of FIGS. 15–18 are particularly well suited for the implantation and/or sizing of vascular grafts. For example, an elongate tubular vascular graft can be positioned on the distal end of the catheter of FIG. 15 and transluminally advanced to the treatment site. As will be understood in the art, the treatment site may be a portion of a vessel having an aneurysm or other wall defect which is desirably spanned by the graft. The graft is preferably expanded by the balloon to a first diameter at the treatment site. The proximal and distal end zones of the graft are preferably expanded to a larger diameter so that they are seated against the vessel wall proximally and distally of the vessel wall defect. The balloon may then be deflated and withdrawn. If the embodiment of FIGS. 17 or 18 is used, the method may additionally include the step of expressing medication or other media at the treatment site. The balloons of the present invention may also be utilized for methods of sizing an already implanted graft and/or infusing medication or other media at the site of a previously implanted graft by positioning the balloon within the implanted graft and repeating the steps described above.

The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

What is claimed is:

1. A balloon catheter, comprising:

an elongate, flexible tubular body having proximal and distal ends;

an inflatable balloon on the distal end of the tubular body; and an inflation lumen extending through the tubular body and communicating with the inflatable balloon;

wherein the balloon has a generally cylindrical first zone inflatable to a first diameter and a generally cylindrical second zone distal to the first zone and inflatable to a second, larger diameter.

2. A balloon catheter as in claim 1, further comprising at least one expansion limiting band on the first zone.

* * * * *